United States Patent

Kuroda et al.

[11] Patent Number: 5,935,746
[45] Date of Patent: *Aug. 10, 1999

[54] ELECTROPHOTOGRAPHIC PHOTOSENSITIVE BODY CONTAINING BUTADIENE-DERIVATIVE

[75] Inventors: Masami Kuroda, Kanagawa; Motohiro Takeshima; Kei Yamaguchi, both of Nagano, all of Japan

[73] Assignee: Fuji Electric Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/879,249

[22] Filed: Jun. 19, 1997

[30] Foreign Application Priority Data

Jun. 21, 1996 [JP] Japan .............................. PA 8-179787
Feb. 27, 1997 [JP] Japan .............................. PA 9-043205

[51] Int. Cl.$^6$ ...................................... G03G 5/04
[52] U.S. Cl. ................... 430/56; 430/58; 430/59; 430/83; 430/133
[58] Field of Search .................. 430/58, 59, 83, 430/56, 133

[56] References Cited

PUBLICATIONS

Diamond, Arthur S. Handbook of Imaging Materials. New York: Marcel–Dekker, Inc. pp. 387–392, 1991.

Primary Examiner—Christopher D. Rodee
Attorney, Agent, or Firm—Morrison Law Firm

[57] ABSTRACT

A photosensitive body comprises a conductive substrate; a photosensitive layer on the conductive substrate, the photosensitive layer includes a charge transport compound wherein the charge transport compound is described by a general formula (I):

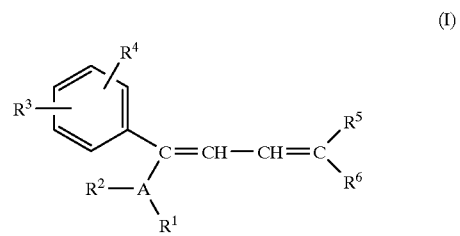

wherein A is a phenyl or naphthyl group; each of $R^1$, $R^2$, $R^3$, and $R^4$ is a hydrogen atom, a halogen atom, an alkyl group with or without substitution, an alkoxy group, an alkylamino group, a nitro group, a cyano group, an aryl group with or without substitution, or a heterocyclic group with or without substitution; and each of $R^5$ and $R^6$ is a cyano group or an alkoxycarbonyl group.

2 Claims, 16 Drawing Sheets

(II-1)

(II-2)

(II-3)

(II-4)

(II-5)

(II-6)

(II-7)

(II-8)

(II-9)

(II-10)

(II-11)

(II-12)

(II-13)

(II-14)

(II-15)

(II-16)

(II-17)

(II-18)

(II-19)

(II-20)

(II-21)

(II-22)

(II-23)

(II-24)

(III-1)

(III-2)

(III-3)

(III-4)

(III-5)

(III-6)

(III-7)

(III-8)

(III-9)

(III-10)

(III-11)

(III-12)

(IV-1)

(IV-2)

(IV-3)

(IV-4)

(IV-5)

(IV-6)

(IV-7)

(V-7)

(V-8)

(V-9)

(V-10)

(V-11)

(V-12)

(V-13)

(V-14)

(V-15)

(V-16)

(V-17)

(V-18)

(V-19)

(V-20)

(V-21)

(V-22)

(V-23)

(V-24)

(V-25)

(V-26)

(V-27)

(V-28)

(V-29)

(V-30)

(V-31)

(V-32)     (V-33)

(V-34)     (V-35)

(V-36)     (V-37)     (V-38)

(V-39)

(V-40)

(V-41)

(V-42)

(V-43)

(V-44)

(V-45)

ELECTROPHOTOGRAPHIC PHOTOSENSITIVE BODY CONTAINING BUTADIENE-DERIVATIVE

BACKGROUND OF THE INVENTION

The present invention relates to an electrophotographic photosensitive body. In particular, the present invention is directed to an electrophotographic photosensitive body used in an electrophotographic device such as, for example, an electrophotographic printer or a copier. The present invention is directed to the improvement of a charge transport substance used for a photosensitive layer.

Conventional photosensitive materials for a electrophotographic photosensitive body (hereafter referred to as "photosensitive body") used for electrophotographic printers, facsimiles, digital copiers, and analog copiers include inorganic photoconductive substances such as selenium or its alloys; inorganic photoconductive substances such as zinc oxide or cadmium sulfide dispersed into resin binding agents; organic photo-conductive substances such as poly-N-vinylcarbazole or polyvinylanthracene, and organic photoconductive substances such as phthalocyanine or bisazo compounds that are dispersed into resin binding agents or vacuum deposited.

The photosensitive body requires properties that serve the functions of retaining surface charges in a dark place, receiving light to generate charges, and receiving light to transport charges. Further, photosensitive bodies can be classified into either single-layer photosensitive bodies having all these functions in a single layer or laminated photosensitive bodies having these functions separated into a layer mainly contributing to the generation of charges and another layer mainly contributing to the retention of surface charges in a dark place and the transfer of charges during the reception of light. Image formation using an electrophotographic method using such a photosensitive body is carried out by, for example, a Carson process. Image formation with this method is carried out by 1) charging a photosensitive body in a dark place using corona discharge, 2) forming on the charged surface of the photosensitive body, electrostatic latent images such as characters or pictures from manuscripts, 3) using toner to develop the electrostatic latent images formed, and 4) settling the developed toner images on a support such as paper. Once the toner images have been transferred, the photosensitive body is reused after static elimination, removal of remaining toner, and photo-static elimination.

Various image formation processes are used for electrophotographic apparatuses that use such a Carson process. The charging process includes a corotron or scorotron method that uses metallic wire and a contact charging method that uses a charging brush or roller. The developing process includes a two-component developing method, a non-magnetic one-component developing method, and a magnetic one-component developing method.

In recent years, electrophotographic photosensitive bodies of organic materials have been put into practical use due to their advantages such as flexibility, thermal stability, and film formation capability. Such photosensitive bodies include, for example, a photosensitive body of poly-N-vinylcarbazole and 2,4,7-trinitroflurenone-9-on (described in U.S. Pat. No. 3,484,237, incorporated herein by reference), a photosensitive body mainly comprising an organic pigment (JP-A-47-37543, incorporated herein by reference), and a photosensitive body mainly comprising an eutectic complex of a dye and a resin (JP-A-47-10785, incorporated herein by reference). Currently, common electrophotographic photosensitive bodies of such organic materials have a function-separated laminated structure in which 1) a charge-generation layer comprising non-metallic phthalocyanine, metallic phthalocyanine such as titanyl phthalocyanine, or an azo compound and a resin binder and 2) a charge—transport layer comprising a hydrozone, styryl, diamine, or butadiene derivative and a resin binder are laminated.

Photosensitive bodies can be charged negatively or positively. Generally, negatively charged photosensitive bodies are disadvantageous compared to positively charged photosensitive bodies. In a negatively charged laminated photosensitive body having a charge generation layer and a charge-transport layer formed on a conductive support (in that order) that also has holes moved due to the properties of the power-supplying charge-transport material so as to become sensitive when the surface is negatively charged, the corona discharge used in such negatively charged laminated photosensitive bodies during charging is unstable compared to positive charging. Furthermore, ozone or nitrogen oxides might be generated that stick to the surface of the photosensitive body, thereby causing physical and chemical degradation and affecting the environment. Thus, positive charging photosensitive bodies with fewer requirements have a wider range of applications and are more generally advantageous than negative charging photosensitive bodies.

As a result, in the prior art, various positive charging photosensitive bodies have been proposed. For example, a method for simultaneously dispersing a charge generation and transport materials into a resin binder to form a single photosensitive layer has been proposed and put into practical use to a limited extent. The sensitivity of this method, however, is insufficient for applications to fast devises and requires further improvement for repeatability. In order to provide a function-separated laminated structure to increase sensitivity, another method laminates a charge-generation layer on a charge-transport layer to form a photosensitive body for positive charging. Since, however, this method forms the charge-generation layer on the surface, the stability during repeated use is not good because of the effects from corona charge, light irradiation, and mechanical wear. In this case, a protective layer formed on the charge-generation layer has been proposed. Nonetheless, however, although this method prevents mechanical wear, it degrades important electrical characteristics such as sensitivity.

Other methods for laminating a charge-transport layer on a charge-generation layer to form a photosensitive body have been proposed using known charge transport materials that include 2,4,7-trinitro-9-fluorenone, but this substance is carcinogenic and thus unsuitable from the viewpoint of safety. In addition, although Japanese KOKAI's 50-131941, 6-59483, and 6-123986 have proposed cyano and quinone compounds, compounds having a sufficient charge-transport function for practical use have not been obtained yet.

As described above, organic materials have many advantages over inorganic materials, but materials having properties that sufficiently meet the requirements for the electrophotographic photosensitive body have not been obtained yet. There is a strong need for highly sensitive photosensitive body products that do not have their properties affected after long-time use in an electrophotographic apparatus. In particular, there is growing market demand for photosensitive bodies that can sufficiently endure long, continuous use in various electrophotographic apparatuses, including various image formation processes such as described above.

Conventional laminated organic photosensitive bodies have various problems to be solved, such as inadequate electrical characteristics such as photosensitivity, decreasing charging potential and sensitivity from extended use, and increasing residual potential from extended use under practical conditions. Thus, techniques that meet all the performance requirements have not been established.

OBJECTS AND SUMMARY OF THE INVENTION

It is an object of the present invention to overcome the limitations of the prior art.

It is an object of this invention to provide a highly sensitive photosensitive body that has sufficient repetition stability to endure long-time continuous use in an actual image formation apparatus.

In particular, it is an object of the present invention to provide a photosensitive body that is compatible with various electrophotographic apparatuses that use corotron and scorotron methods, various charging processes such as contact-charging methods using a charging brush or roller, and various developing processes such as two-component, non-magnetic one-component, and magnetic one-component developing methods, as described above.

It is another object of this invention to provide a highly sensitive electrophotographic photosensitive body for copiers and printers that can be used with positive charging and that has excellent electrical characteristics.

As a result of their efforts to achieve the above objects, the inventors have found that they can be achieved by including at least one type of specific butadiene derivative in a photosensitive layer of an electrophotographic photosensitive body as a charge transport substance.

An electrophotographic photosensitive body according to the present invention is characterized by including at least one type of butadiene derivative as a charge-transport substance with a photosensitive layer formed on a conductive substrate shown by a general formula (I):

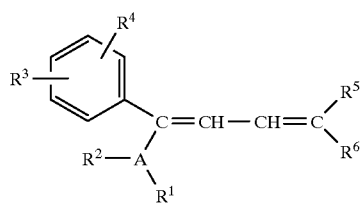

(I)

wherein:

A indicates a phenyl or naphthyl group which can be substituted by $R^1$ and/or $R^2$;

$R^1$, $R^2$, $R^3$, and $R^4$ may be identical to or different from each other and each denotes a hydrogen atom, a halogen atom, an alkyl group with or without substitution, an alkoxy group, an alkylamino group, a nitro group, a cyano group, an aryl group with or without substitution, or a heterocyclic group with or without substitution; and $R^5$ and $R^6$ may be identical to or different from each other and each denotes a cyano group or an alkoxycarbonyl group.

According to the present invention, the alkyl, alkoxy, and alkylamino groups in $R^1$ to $R^4$ in Formula I preferably have one to eight carbons each.

According to the present invention, substituents for substituted alkyls include halogen atoms; aryl groups such as, for example, phenyl groups; and heterocyclic groups such as, for example, thienyl groups.

According to the present invention, substituents for substituted heterocyclics include halogen atoms; alkyl groups such as, for example, methyl groups and ethyl groups; aryl groups such as, for example, phenyl groups; and heterocyclic groups such as, for example, thienyl groups.

According to the present invention, substituents for substituted aryls include halogen atoms; alkyl groups such as, for example, methyl groups and ethyl groups, amino groups such as, for example, dialkylamino groups; aryl groups such as, for example, phenyl groups; and heterocyclic groups such as, for example, thienyl groups.

No conventional electrophotographic photosensitive bodies use the butadiene derivative shown by Formula I as a photosensitive layer. To achieve the above objects, the inventors have carefully examined various organic materials and conducted many experiments on such butadiene derivatives to obtain the following results, although a full explanation is not fully yet available.

When repeatedly used in various electrophotographic apparatuses, including various image-formation processes such as described above, the photosensitive body of the present invention maintains high sensitivity and is not subjected to variations in potential or sensitivity over time. In other words, excellent photosensitive characteristics are maintained by adding the butadiene derivative shown by Formula (I) to the system being used.

In addition, by using as a charge-transport substance the butadiene derivative of the specific skeleton shown by Formula (I), a highly sensitive photosensitive body that can be used with positive charging and that has excellent electrical characteristics is obtained.

Briefly stated, a photosensitive body comprises a conductive substrate; a photosensitive layer on the conductive substrate, the photosensitive layer includes a charge transport compound wherein the charge transport compound is described by a general formula (I):

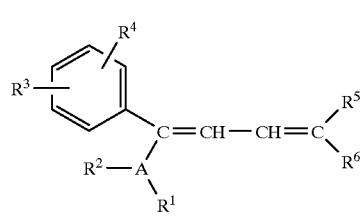

(I)

wherein A is a phenyl or naphthyl group; each of $R^1$, $R^2$, $R^3$, and $R^4$ is a hydrogen atom, a halogen atom, an alkyl group with or without substitution, an alkoxy group, an alkylamino group, a nitro group, a cyano group, an aryl group with or without substitution, or a heterocyclic group with or without substitution; and each of $R^5$ and $R^6$ is a cyano group or an alkoxycarbonyl group.

According to an embodiment of the present invention, a charge transport compound in a photosensitive body, wherein the charge transport compound is described by a general formula (I):

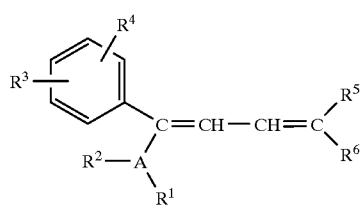

(I)

wherein A is a phenyl or naphthyl group; $R^1$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^2$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^3$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^4$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^5$ is a cyano group or an alkoxycarbonyl group; and $R^6$ is a cyano group or an alkoxycarbonyl group.

According to the present invention, substituents for substituted alkyls include halogen atoms; aryl groups such as, for example, phenyl groups; and heterocyclic groups such as, for example, thienyl groups.

According to the present invention, substituents for substituted heterocyclics include halogen atoms; alkyl groups such as, for example, methyl groups and ethyl groups; aryl groups such as, for example, phenyl groups; and heterocyclic groups such as, for example, thienyl groups.

According to the present invention, substituents for substituted aryls include halogen atoms; alkyl groups such as, for example, methyl groups and ethyl groups, amino groups such as, for example, dialkylamino groups; aryl groups such as, for example, phenyl groups; and heterocyclic groups such as, for example, thienyl groups.

According to another embodiment of the present invention, a photosensitive body comprises a conductive substrate; a photosensitive layer on the conductive substrate, the photosensitive layer includes a charge transport compound wherein the charge transport compound is described by a general formula (I):

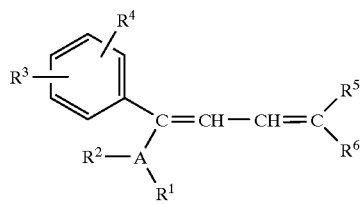

(I)

wherein A is a phenyl or naphthyl group; $R^1$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^2$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^3$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^4$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^5$ is a cyano group or an alkoxycarbonyl group; and $R^6$ is a cyano group or an alkoxycarbonyl group.

According to an embodiment of the present invention, a method to make a photosensitive body by forming a photosensitive layer on a substrate, the photosensitive layer includes a charge transport compound wherein the charge transport compound is described by a general formula (I):

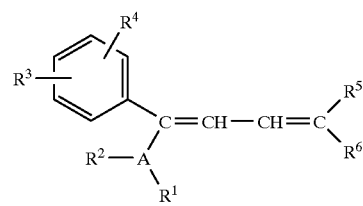

(I)

wherein A is a phenyl or naphthyl group; $R^1$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^2$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^3$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^4$ is a hydrogen atom, a halogen atom, an alkyl group with or without substitution, an alkoxy group, an alkylamino group, a nitro group, a cyano group, an aryl group with or without substitution, or a heterocyclic group with or without substitution; $R^5$ is a cyano group or an alkoxycarbonyl group; and $R^6$ is a cyano group or an alkoxycarbonyl group.

According to the present invention, substituents for substituted alkyls include halogen atoms; aryl groups such as, for example, phenyl groups; and heterocyclic groups such as, for example, thienyl groups.

According to the present invention, substituents for substituted heterocyclics include halogen atoms; alkyl groups such as, for example, methyl groups and ethyl groups; aryl groups such as, for example, phenyl groups; and heterocyclic groups such as, for example, thienyl groups.

According to the present invention, substituents for substituted aryls include halogen atoms; alkyl groups such as, for example, methyl groups and ethyl groups, amino groups such as, for example, dialkylamino groups; aryl groups such as, for example, phenyl groups; and heterocyclic groups such as, for example, thienyl groups.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Butadiene derivatives shown by Formula (I) which are used for this invention are synthesized by conventional methods.

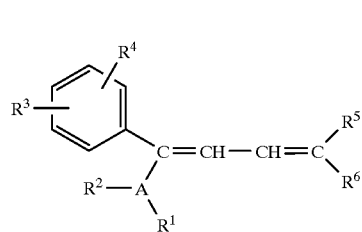

(I)

wherein:

A indicates a phenyl or naphthyl group which can be substituted by $R^1$ and/or $R^2$;

$R^1$, $R^2$, $R^3$, and $R^4$ may be identical to or different from each other and each denotes a hydrogen atom, a halogen atom, an alkyl group with or without substitution, an alkoxy group, an alkylamino group, a nitro group, a cyano group, an aryl group with or without substitution, or a heterocyclic group with or without substitution; and $R^5$ and $R^6$ may be identical to or different from each other and each denotes a cyano group or an alkoxycarbonyl group.

According to the present invention, the alkyl, alkoxy, and alkylamino groups in $R^1$ to $R^4$ in Formula I preferably have one to eight carbons each.

According to the present invention, substituents for substituted alkyls include halogen atoms; aryl groups such as, for example, phenyl groups; and heterocyclic groups such as, for example, thienyl groups.

According to the present invention, substituents for substituted heterocyclics include halogen atoms; alkyl groups such as, for example, methyl groups and ethyl groups; aryl groups such as, for example, phenyl groups; and heterocyclic groups such as, for example, thienyl groups.

According to the present invention, substituents for substituted aryls include halogen atoms; alkyl groups such as, for example, methyl groups and ethyl groups, amino groups such as, for example, dialkylamino groups; aryl groups such as, for example, phenyl groups; and heterocyclic groups such as, for example, thienyl groups.

In other words, the compound according to Formula (I) can be synthesized easily by allowing an aldehyde described by Structural Formula (Ia)

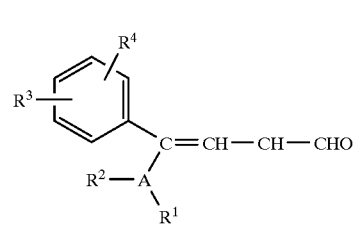

(Ia)

to react with a reagent described by Structural Formula (Ib)

(Ib)

in an appropriate organic solvent, for example, benzene or toluene in the presence of an alkali.

Figure 4:
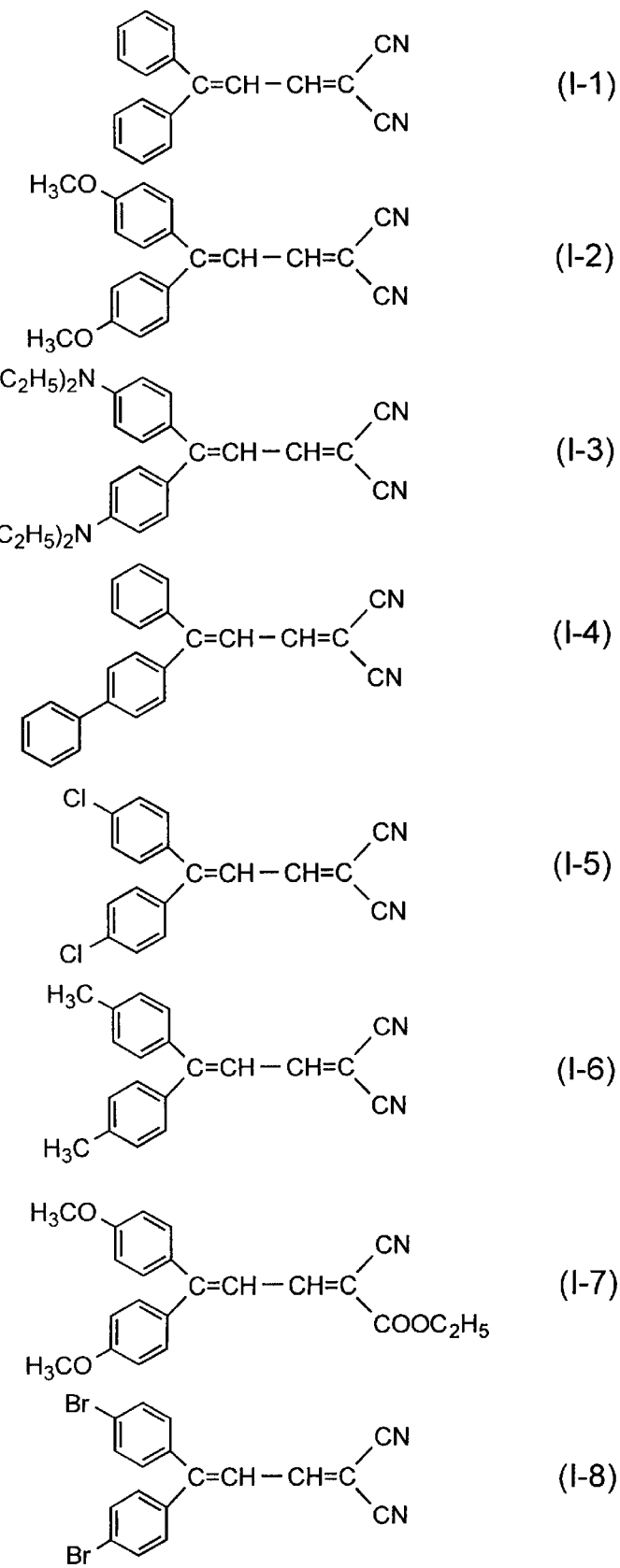
FIG. 4 are specific examples of butadiene derivatives according to Formula (I) of the present invention.
Figure 5:
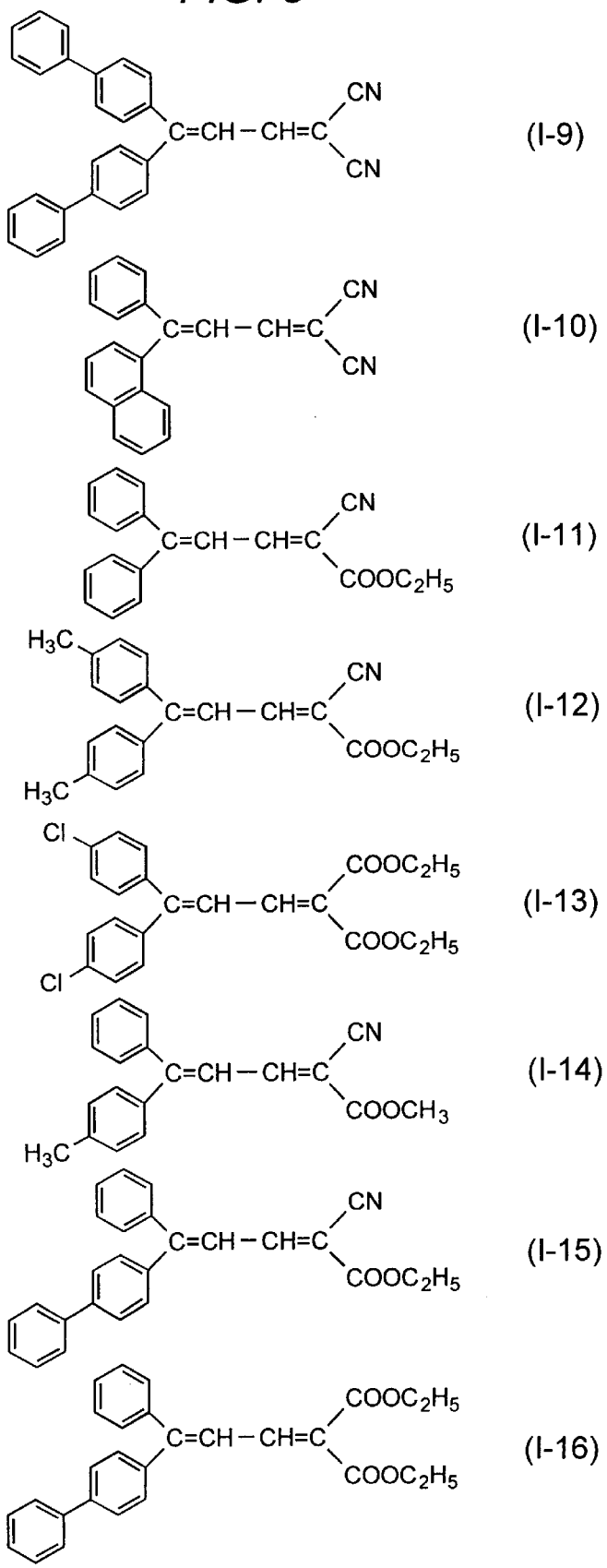
FIG. 5 are specific examples of butadiene derivatives according to Formula (I) of the present invention.

Specific examples of butadiene derivatives according to Formula (I) which are obtained in the above manner are shown in FIG. 4 and FIG. 5.

Figure 6:
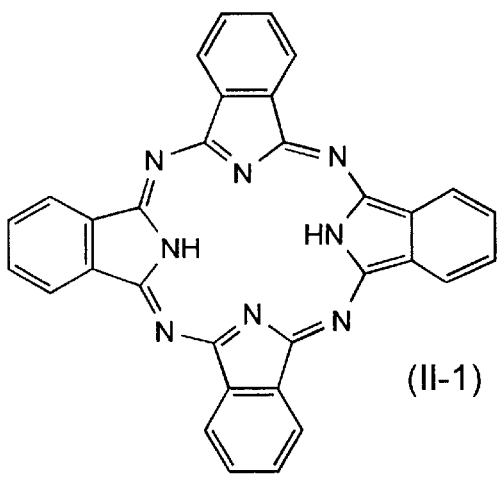
FIG. 6 are specific examples of phthalocyanine compounds for charge generation substances for the photosensitive body of the present invention.
Figure 6:
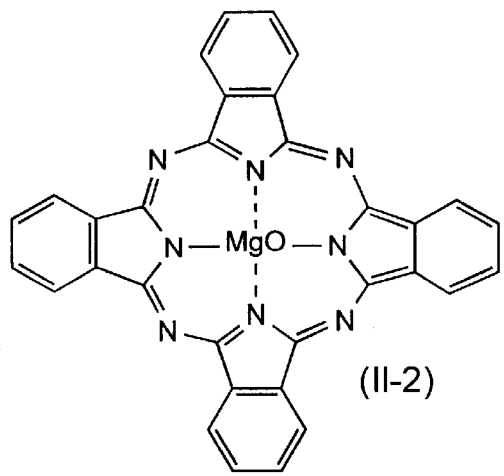
Figure 6:
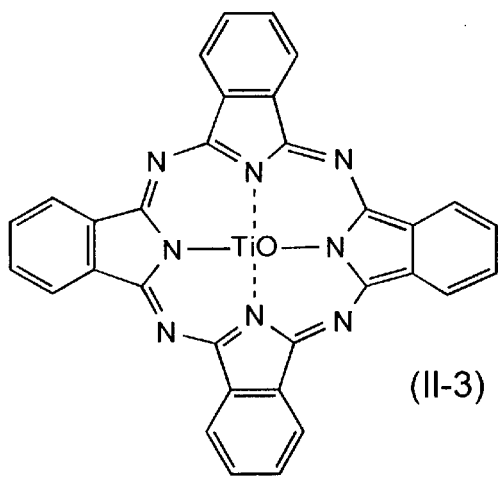
Figure 6:
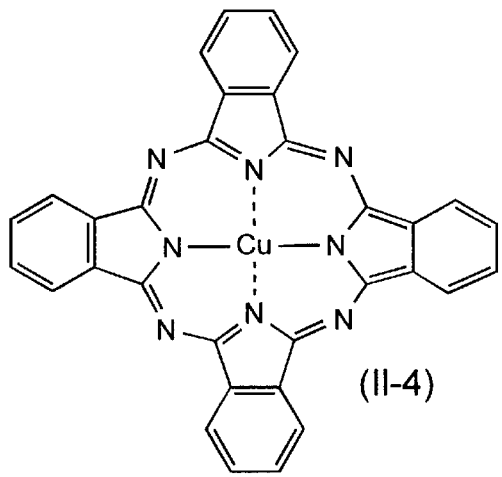
Figure 6:
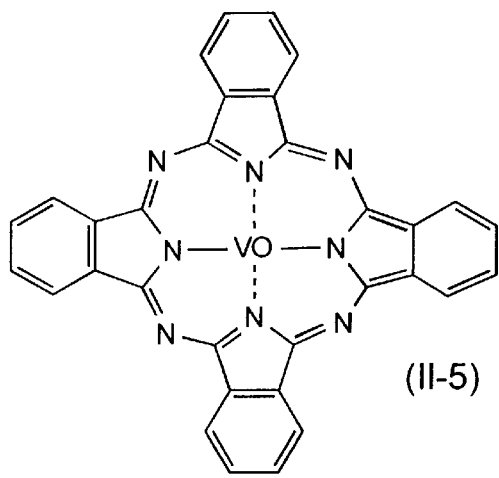
Figure 6:
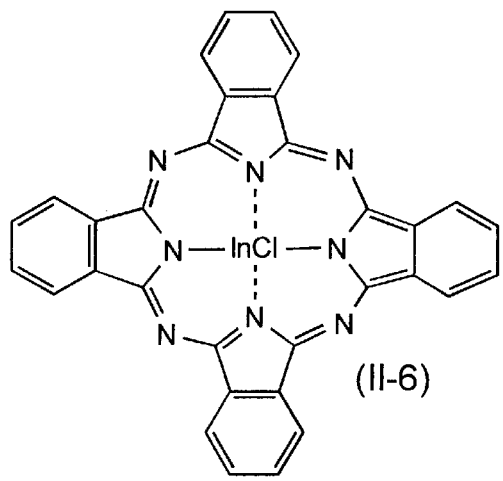
Figure 7:
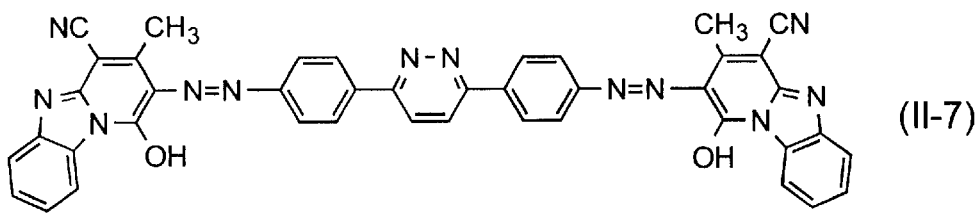
FIG. 7 are specific examples of azo compounds for charge generation substances for the photosensitive body of the present invention.
Figure 7:
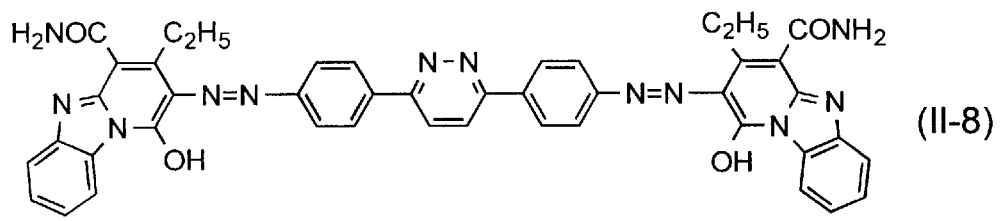
Figure 7:
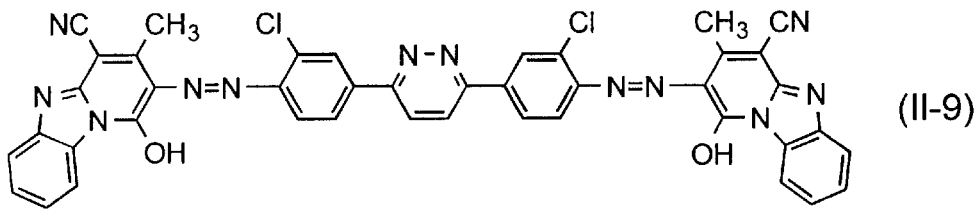
Figure 7:
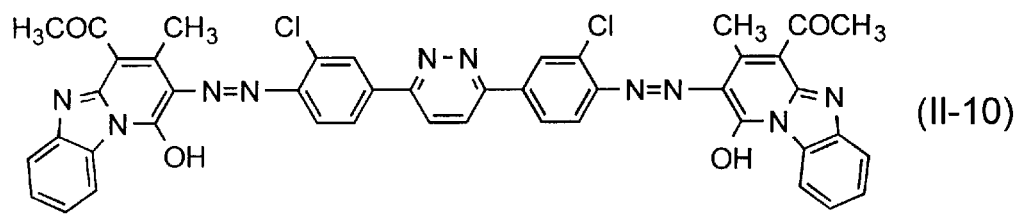
Figure 7:
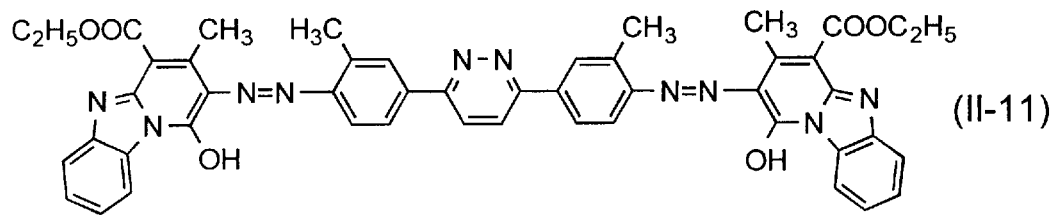
Figure 7:
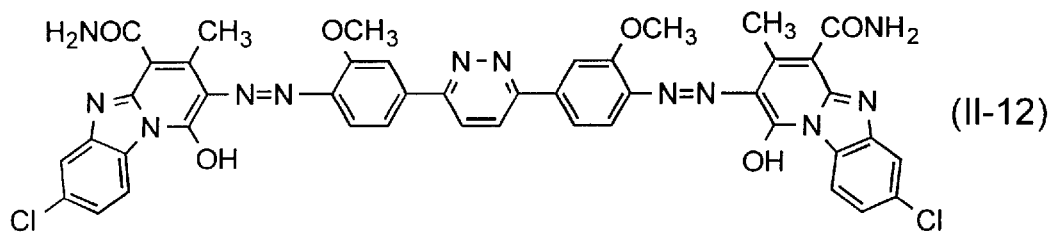
Figure 8:
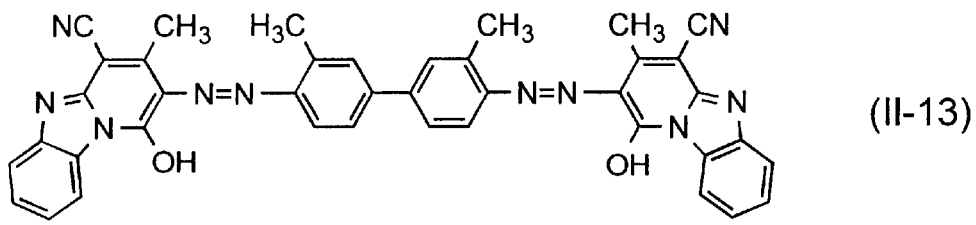
FIG. 8 are specific examples of azo compounds for charge generation substances for the photosensitive body of the present invention.
Figure 8:
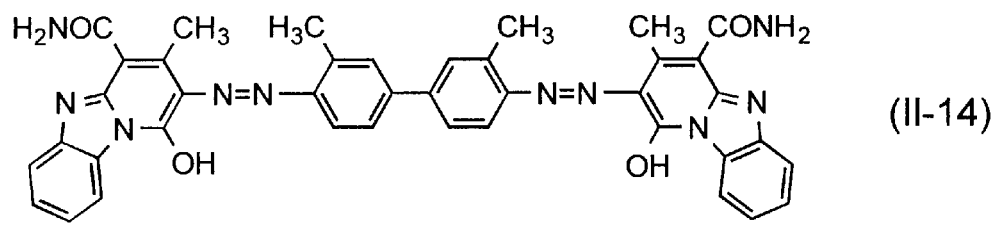
Figure 8:
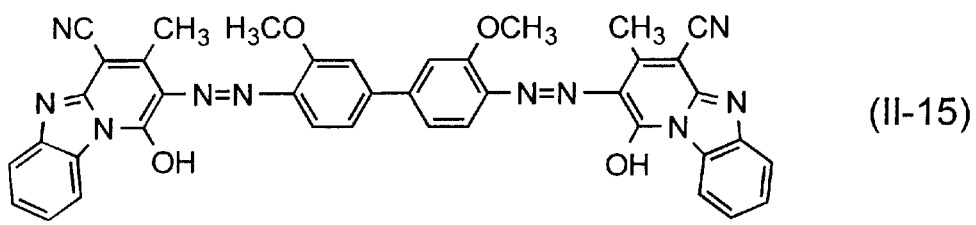
Figure 8:
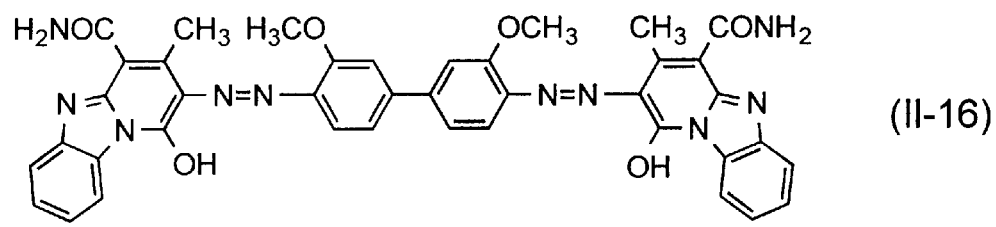
Figure 8:
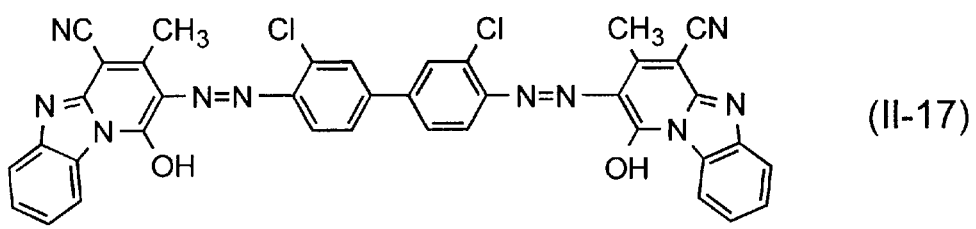
Figure 8:
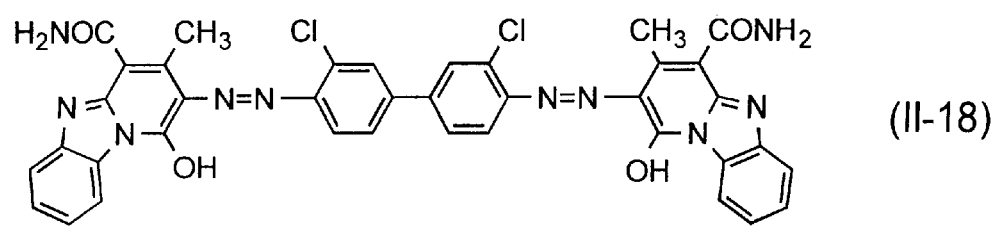
Figure 9:
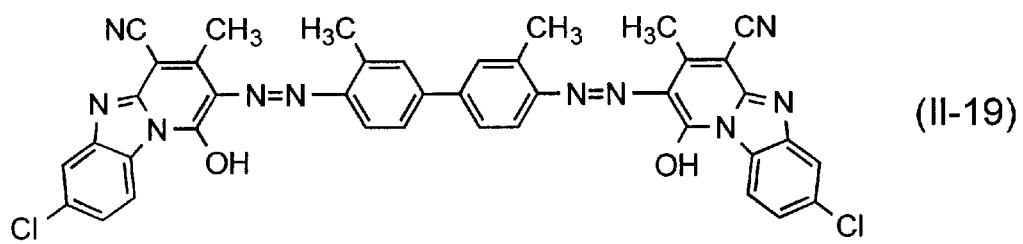
FIG. 9 are specific examples of azo compounds for charge generation substances for the photosensitive body of the present invention.
Figure 9:
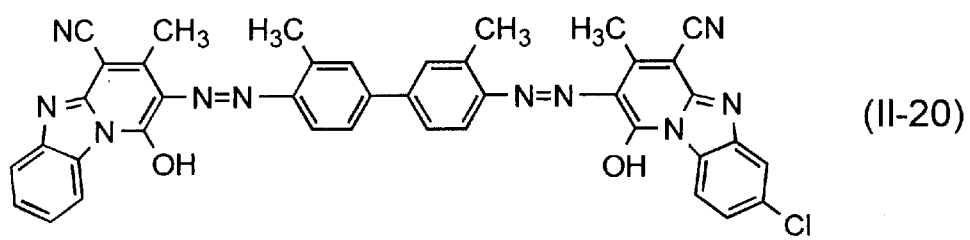
Figure 9:
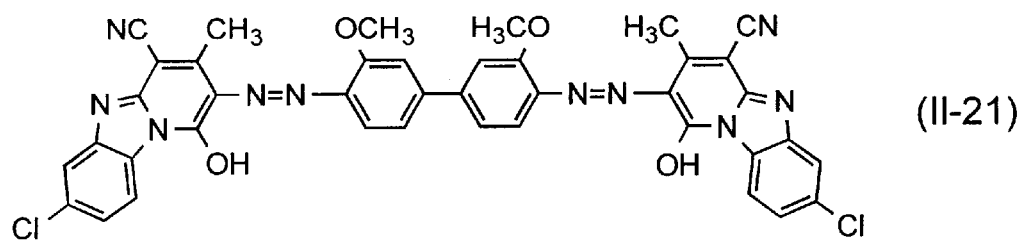
Figure 9:
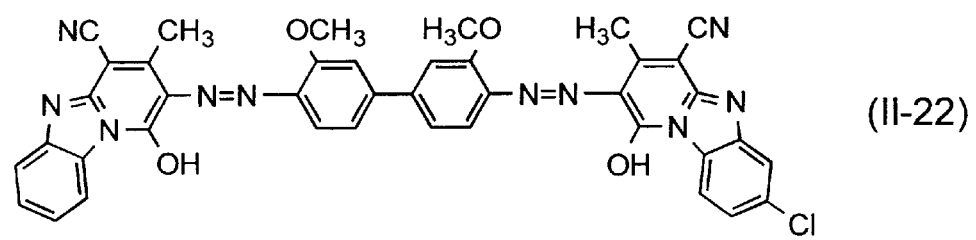
Figure 9:
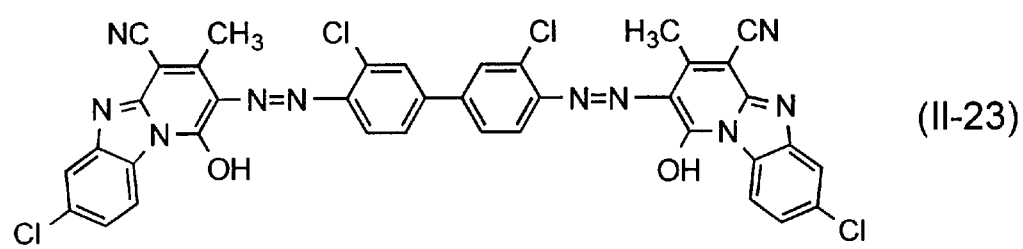
Figure 9:
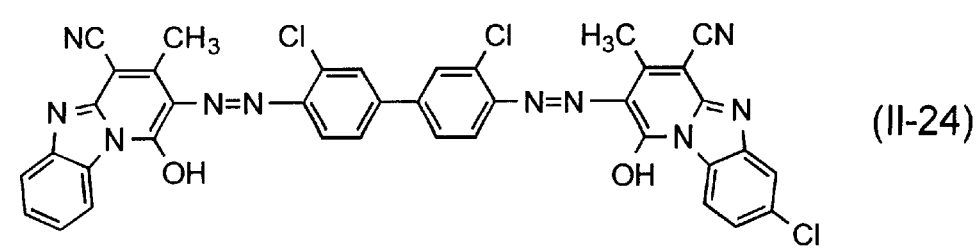

Charge generation substances that can be used in this invention include the various phthalocyanine compounds shown in FIG. 6 as specific examples (II-1) to (II-6), the azo compounds shown in FIGS. 7–9 as specific examples (II-7) to (II-24), and derivatives thereof. In addition, this invention allows the use of a combination of the butadiene derivative shown by Formula (I) and the various compounds shown in FIG. 10 and 11 as specific examples (III-1) to (III-12). Resin binders for the charge transport layer include the various polycarbonates shown in FIG. 12 as specific examples (IV-1) to (IV-7). Various antioxidants such as an amine, phenol, sulfur, phosphite, phosphorous, and benzopinacol systems can be used in the photosensitive layer to prevent ozone degradation that obstructs the use of the photosensitive body. Specific Examples (V-1) to (V-45) of such antioxidants are shown in FIGS. 13–18.

The photosensitive body according to the present invention contains the above compounds in the photosensitive layer. The present invention is described below with reference to the cross-sectional view shown in FIGS. 1 to 3.

Figure 1:
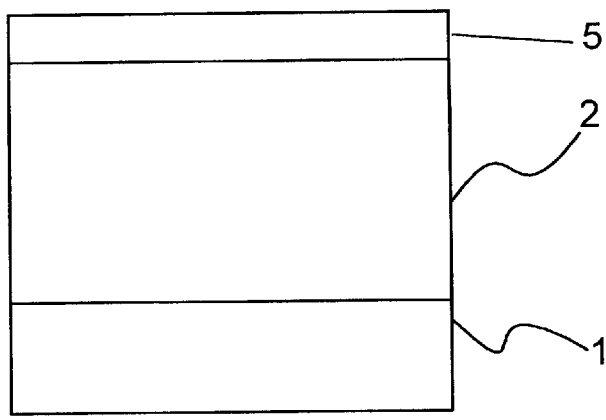
FIG. 1 is a cross-sectional view of a single-layer photosensitive body according to the present invention.
Figure 2:
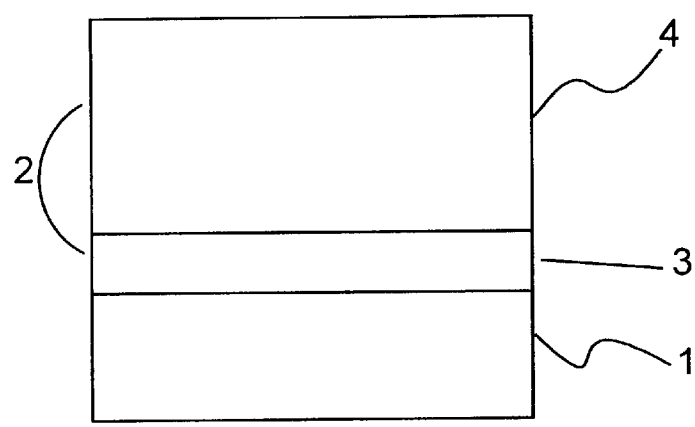
FIG. 2 is a cross-sectional view of a laminated photosensitive body according to the present invention.
Figure 3:
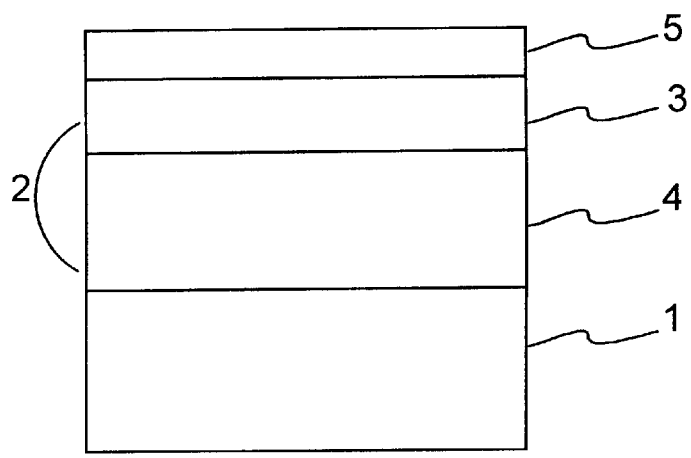
FIG. 3 is a cross-sectional view of a laminated photosensitive body according to another embodiment of the present invention.

FIG. 1 is a cross-sectional view showing a single-layer photosensitive body according to one embodiment of this invention. FIG. 2 is a cross-sectional view showing a laminated photosensitive body according to another embodiment of this invention. FIG. 3 is a cross-sectional view showing a laminated photosensitive body according to yet another embodiment of this invention.

The butadiene derivative in the present invention performs either (a) as a major charge transport material or (b) as one of additives in a charge transport layer as an electron transport substance. In the case of (a), the butadiene derivative is preferably contained at 30–70 wt %, more preferably 40–60 wt % in a charge transport layer. In the case of (b), the butadiene derivative is contained at preferably 0.5–5 wt % in a charge transport layer. In the case of (a), a single layered photosensitive body (FIG. 1) and a laminated photosensitive body of the type substrate/charge generation layer/charge transport layer (FIG. 2) are of a positive charging type. In the case of (b), a single layered photosensitive body (FIG. 1) and a laminated photosensitive body of the type substrate/charge transport layer/charge generation layer (FIG. 3) are of a positive charging type, but, a laminated photosensitive body of the type substrate/charge generation layer/charge transport layer (FIG. 2) is of a negative charging type.

FIG. 1 shows a photosensitive body including a photosensitive layer 2 formed on a conductive substrate 1 in which a charge-generation material and a butadiene derivative that is a charge-transport material are together dispersed into a resin binder, and further including a coating layer 5 as required. This configuration is normally called a single layer photosensitive body.

FIG. 2 shows a photosensitive body comprising a photosensitive multilayer 2 comprising charge-generation layer 3 mainly consisting of a charge-generation material and charge-transport layer 4 containing a butadiene derivative that is a charge-transport substance, the layers of which are laminated onto conductive substrate 1. This configuration is normally called a laminated photosensitive body.

FIG. 3 shows a photosensitive body having a layer constitution opposite to that shown in FIG. 2. In this case, charge-transport layer 4 is laminated onto conductive substrate 1, while charge-generation layer 3 is laminated onto charge-transport layer 4. It is preferred that coating layer 5 is formed to protect the charge-generation layer 3.

The photosensitive body shown in FIG. 1 can be produced, for example, by dispersing the charge-generation substance into a solution of the charge-transport substance and a resin binder, then coating the dispersed solution onto the conductive substrate. The coating layer may further be coated and formed as required.

The photosensitive body shown in FIG. 2 can be produced, for example, by vacuum depositing the charge-generation substance on to the conductive substrate or coating and drying the substrate with a dispersed solution in which particles of the charge-generation substance are dispersed into a solvent or resin binder and coating and drying the surface of the layer obtained with a solution of the charge-transport material and a resin binder.

The photosensitive body shown in FIG. 3 can be produced, for example, by coating and drying the conductive substrate 1 with a solution of the charge-transport substance and a resin binder and vacuum depositing the charge-generation substance thereon, or coating and drying the substrate with a dispersed solution in which particles of the charge-generation substance are dispersed into a solvent and resin binder and further forming the coating layer 5.

Conductive substrate 1 acts as an electrode for the photosensitive body and further constitutes a support for the other layers. Conductive substrate 1 may be a cylinder, a plate, or a film, and comprises metal such as aluminum, stainless steel, or nickel. Conductive substrate 1 can further comprise glass or resin which is subjected to conduction processing as a material. Polymeric dispersion film materials used for surface modification for the conduction processing include insulating polymers such as casein, polyvinyl alcohol, nylon, polyamide, melamine, and cellulose; conductive polymers such as polythiophene, polypyrrole, and polyaniline; and these polymers containing added metal oxide powders or low molecular weight compounds.

Charge-generation layer 3 is formed, for example, by coating a material in which particles of the charge-generation substance are dispersed in the resin binder or carrying out vacuum deposition as described above, and receives light to generate charges. Charge-generation layer 3 must have high charge-generation efficiency and be able to smoothly inject charges generated into the charge-transport layer 4. Charge-generation layer 3 preferably has little dependence on electric fields and provides good injection even with low electric fields.

Charge-generation substances include various phthalocyanine compounds shown in FIG. 6 as specific examples (II-1) to (II-6); the azo compounds shown in FIGS. 7–9 as (II-7) to (II-24); and derivatives thereof, as well as phthalocyanine compounds such as titanyl phthalocyanine; pigments or dyes such as quinone, indigo, cyanine, squarrylium, azlenium, and pyrylium compounds; and selenium or its compounds. A preferred substance can be selected depending on the light wavelength region of the exposure light source used for image formation.

Charge-generation layer 3 is only required to have a charge-generation function, so its thickness is determined by the light-absorption coefficient of the charge-generation substance, generally 5 $\mu$m or less, preferably 2 $\mu$m or less. Charge-generation layer 3 may mainly comprise the charge-generation substance with the addition of the charge-transport substance.

Resin binders for charge-generation layer 3 include polycarbonate, polyester, polyamide, polyurethane, epoxy resin, polyvinylbutyral, polyvinylacetal, phenoxy resin, silicone resin, acryl resin, vinyl chloride resin, vinylidene chloride resin, vinyl acetate resin, homal resin, cellulose resin, copolymers thereof, halides thereof, and cyanoethyl compounds, which may be used individually or in combination.

Charge-transport layer 4 is a paint film in which the butadiene derivative shown by Formula (I) is dispersed into the resin binder as the charge-transport substance. Charge-transport layer 4 can retain charges for the photosensitive layer in a dark place as an insulating layer and transport charges injected from charge-generation layer 3 during the reception of light. The charge-transport material may comprise a combination of any of the various compounds shown in FIGS. 10 and 11 as specific examples (III-1) to (III-12).

Charge-transport layer 4 preferably has a thickness of 10 to 40 μm. Resin binders for charge transport include polymers and copolymers of the various polycarbonates shown in FIG. 12 as specific examples (IV-1) to (IV-7), polystyrene, polyacrylate, polyphenyleneetheracryl, polyester, and methacryl acid ester.

In addition, antioxidants such as amine, phenol, sulfur, phosphorous ester, and phosphorous systems as shown in FIGS. 13–18 as specific examples (V-1) to (V-45) can be contained in charge-transport layer 4 to prevent ozone degradation that obstructs the use of the obtained photosensitive body.

Coating layer 5 can receive and retain charges from corona discharge in a dark place and transmit light that is sensed by the photosensitive layer. During exposure, coating layer 5 must also transmit light to allow it to reach the photosensitive layer and receive charges generated and injected to neutralize and eliminate the charges on the surface. The coating material includes organic insulating film formation materials such as polyester and polyamide. The coating material may comprise mixtures of organic materials and inorganic materials such as glass resin and $SiO_2$ or materials such as metals and metal oxides that can reduce electric resistance.

As described above, the covering material is preferably as transparent as possible in the wavelength region in which the light absorption of the charge-generation substance is at a maximum. The thickness of the coating layer depends on the blending and composition of the coating layer but may be arbitrarily set as long as adverse effects such as an increase in residual potential during repeated use can be prevented.

This invention is specifically described below based on embodiments.

Embodiments 1 to 8

According to Embodiments 1 to 8, various laminated photosensitive bodies with positive charging were produced.

Embodiment 1

Using a mixer, 20 pts.wt. of x-type non-metallic phthalocyanine (hereafter referred to as $H_2Pc$) and 100 pts.wt. of a butadiene derivative shown by Structural Formula (I-1) were kneaded with 100 pts.wt. of polyester resin (Byron 200 manufactured by Toyobo Co., Ltd.) and a tetrahydrofuran solvent for three hours to provide a coating liquid. The coating liquid was then coated onto an aluminum drum with an outer diameter of 30 mm and a length of 260 mm, which is a conductive substrate, to produce a photosensitive body with a coating thickness of 10 μm after drying.

Embodiment 2

Using a mixer, 70 pts.wt. of titanyl phthalocyanine (hereafter referred to as TiOPc) and 30 pts.wt. of vinyl chloride copolymer (MR-110 manufactured by Nippon Zeon Co., Ltd.) was kneaded with methylene chloride for three hours to provide a coating liquid. The coating liquid was then coated onto an aluminum support that is a conductive substrate so as to have a coating thickness of about 1 μm, thereby forming a charge-generation layer. Next, 100 pts.wt. of a butadiene derivative shown by Structural Formula (I-2), 100 pts.wt. of polycarbonate resin (PCZ-200 manufactured by Mitsubishi Gas Chemical Co., Inc.), and 0.1 pts.wt. of silicone oil (type KP-340 supplied by Shinetsu Silicone Co., Ltd.) were mixed with methylene chloride. The mixture was then coated onto the charge-generation layer so as to have a mixture coating thickness of about 10 μm, thereby forming a charge-transport layer.

Embodiment 3

A photosensitive body was produced in the same manner as in Embodiment 2, except that the squarrylium pigment shown by the following structural formula,

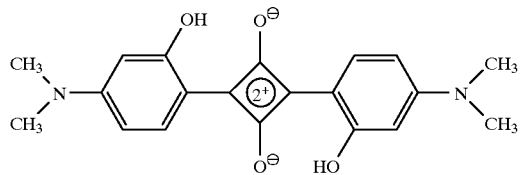

was used instead of TiOPc and the butadiene derivative shown by Structural. Formula (I-3) was used as the charge-transport substance instead of Structural Formula (I-2).

Embodiment 4

A photosensitive body was produced in the same manner as in Embodiment 2 except that the bisazo pigment shown by the following structural formula,

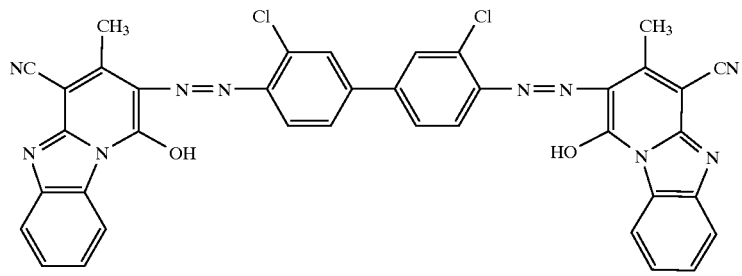

was used instead of TiOPc, the butadiene derivative shown by Structural Formula (I-1) was used as the charge-transport substance, and the polycarbonate resin comprised BP-PC manufactured by Idemitsu Kosan Co., Ltd.

Embodiment 5

A photosensitive body was produced in the same manner as in Embodiment 4 except that the butadiene derivative shown by Structural Formula (I-4) was used as the charge-transport substance.

Embodiment 6

A photosensitive body was produced in the same manner as in Embodiment 4 except that the butadiene derivative shown by Structural Formula (I-5) was used as the charge-transport substance.

Embodiment 7

A photosensitive body was produced in the same manner as in Embodiment 4 except that the butadiene derivative shown by Structural Formula (I-2) was used as the charge-transport substance.

Embodiment 8

A photosensitive body was produced in the same manner as in Embodiment 4 except that the bisazo pigment shown by the following structural formula,

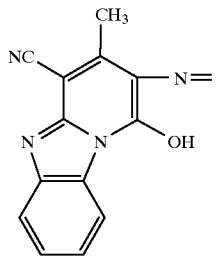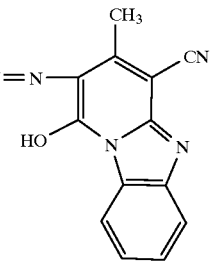

was used instead of the bisazo pigment in Embodiment 4 and the butadiene derivative shown by Structural Formula (I-4) was used as the charge-transport substance.

The electrophotographic characteristics of the photosensitive bodies obtained in the above manner were measured.

The initial surface potential of the photosensitive body positively charged by +4.5 kV corona discharge in a dark place is referred to as Vs (V). With corona discharge suspended, the surface potential Vd (V) after the retention of the photosensitive body in a dark place for five seconds was measured, and the time (seconds) until Vd decreased to half when the surface of the photosensitive body was irradiated with white light at an illumination of 100 lx was determined as sensitivity $E_{1/2}$ (lux•S). The surface potential obtained when the photosensitive body was irradiated with white light at an illumination of 100 lx for ten seconds was referred to as residual potential Vr (V).

In addition, Embodiments 1, 2, and 3 were expected to provide high sensitivity with light of a long wavelength, so the electrophotographic characteristics were simultaneously measured while using monochromatic light with a wavelength of 780 nm. Similar measurements were made up to Vd, and the photosensitive bodies were then irradiated with 1 µW monochromatic light (780 nm) instead of white light to determine the half-value exposure (µJ/cm$^2$). In addition, the residual potential Vr was measured when the surfaces of the photosensitive bodies were irradiated with this light for 10 seconds. The results are shown in Table 1.

TABLE 1

| | White light | | 780 nm monochromatic light | |
|---|---|---|---|---|
| | Sensitivity $E_{1/2}$ (lux · S) | Residual potential (V) | Half-value exposure (µJ/cm$^2$) | Residual potential (V) |
| Embodiment 1 | 10.3 | 60 | 8.8 | 80 |
| Embodiment 2 | 5.4 | 80 | 5.9 | 90 |
| Embodiment 3 | 8.3 | 100 | 12.4 | 60 |
| Embodiment 4 | 9.2 | 50 | — | — |
| Embodiment 5 | 9.5 | 70 | — | — |
| Embodiment 6 | 6.8 | 80 | — | — |
| Embodiment 7 | 7.5 | 40 | — | — |
| Embodiment 8 | 12.7 | 120 | — | — |

Embodiments 9 to 24, Comparative Examples 1 to 5

In the following embodiments and comparative examples, various laminated photosensitive bodies with negative charges were produced. In addition, in the following embodiments and comparative examples, cylindrical aluminum substrates with a thickness of 1 mm, a length of 310 mm, and an outer diameter of 60 mm were washed and dried before use as conductive substrates.

Embodiment 9

Ten pts.wt. of alcohol-soluble copolymeric polyamide resin (CM8000 manufactured by Toray Industries, Inc.) was dissolved into a solvent comprising a mixture of 45 pts.wt. of methanol and 45 pts.wt. of methylene chloride, and the prepared resin film coating liquid was dipped and coated onto the surface of the above cylindrical aluminum substrate, which was then dried at 90° C. for 30 minutes to form an intermediate layer comprising a 0.1 µm resin film.

Next, 1 pts.wt. of polyvinylacetal resin (Ethlek KS-1 manufactured by Sekisui Chemical Co., Inc.) and 1 pts.wt. of bisazo compound shown in FIG. 8 as specific example II-17 as the charge-generation substance were mixed with 150 pts.wt. of methylethylketone and dispersed for 48 hours using a ball mill. The coating liquid obtained was dipped and coated onto the above intermediate layer, which was then dried at 90° C. for 30 minutes to form a charge-generation layer comprising a 0.2 µm resin film.

Figure 10:
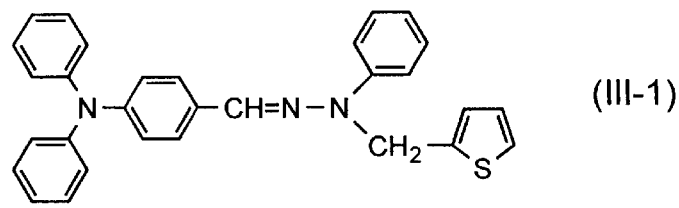
FIG. 10 are specific examples of compounds that are used in combination with the butadiene derivatives of Formula (I) according to the present invention.
Figure 10:
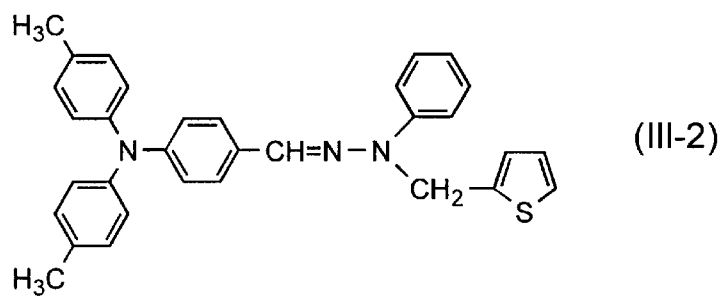
Figure 10:
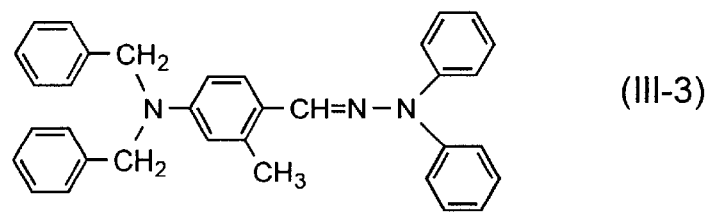
Figure 10:
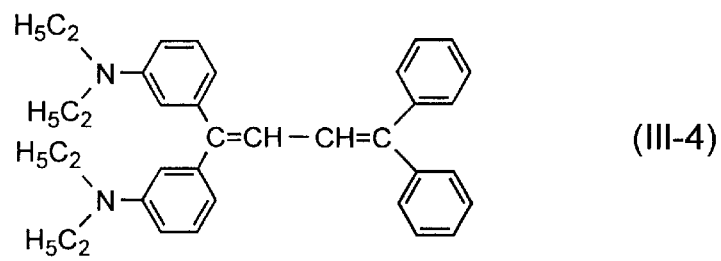
Figure 10:
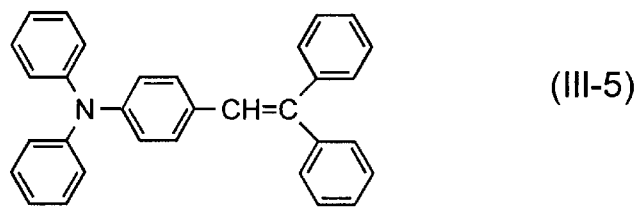
Figure 10:
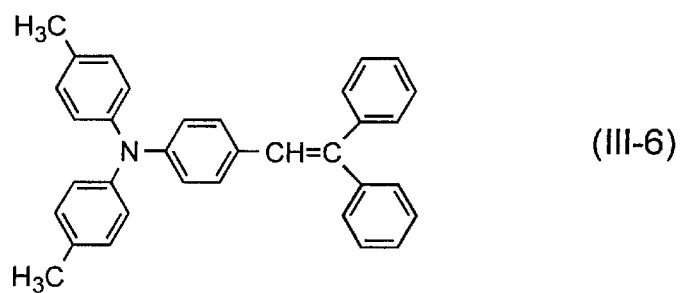
Figure 13:
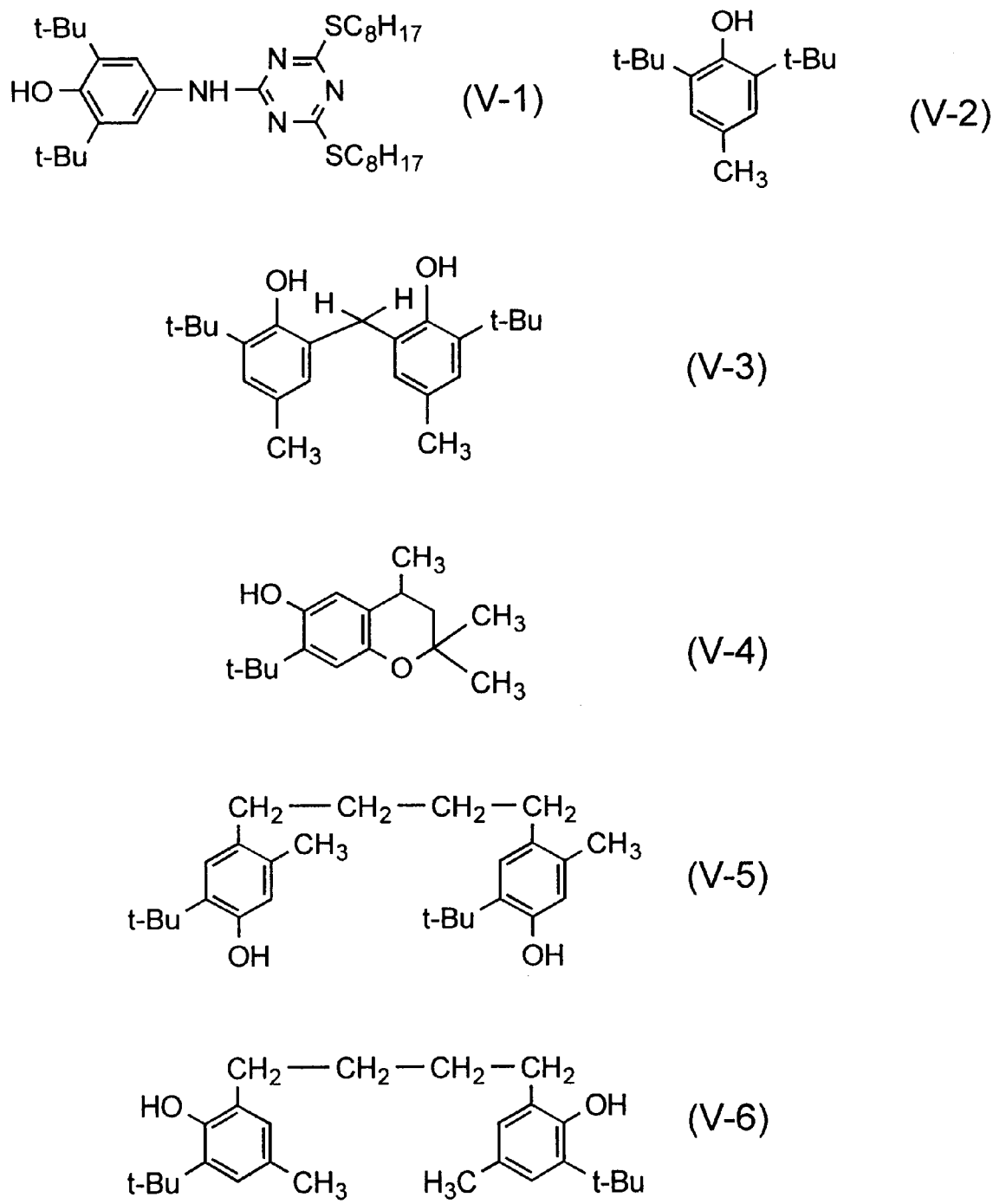
FIG. 13 are specific examples of antioxidants for the photosensitive body of the present invention.
Figure 14:
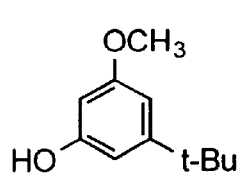
FIG. 14 are specific examples of antioxidants for the photosensitive body of the present invention.
Figure 14:
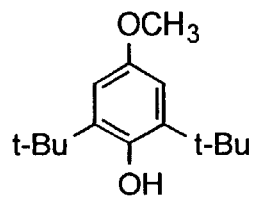
Figure 14:
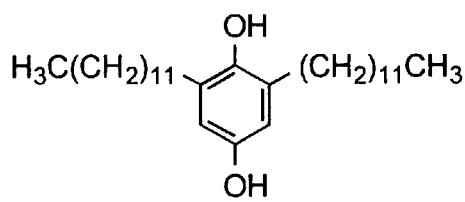
Figure 14:
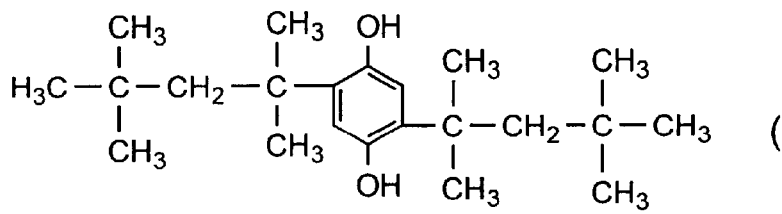
Figure 14:
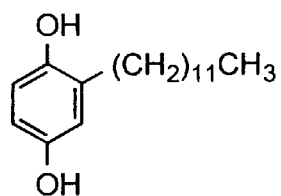
Figure 14:
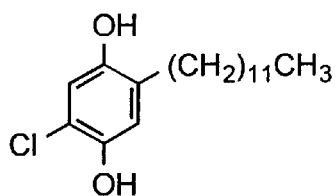
Figure 14:
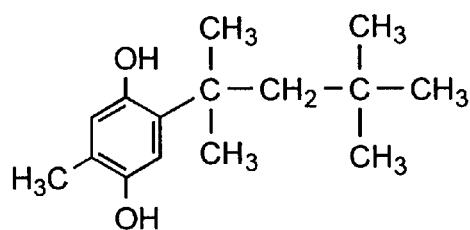
Figure 14:
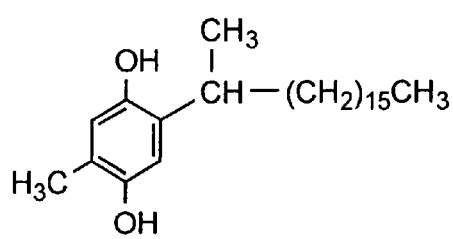
Figure 15:
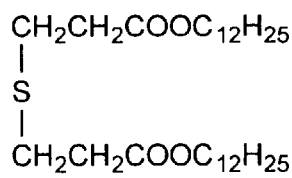
FIG. 15 are specific examples of antioxidants for the photosensitive body of the present invention.
Figure 15:
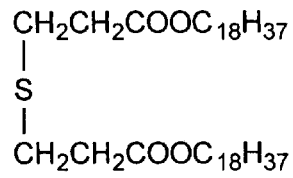
Figure 15:
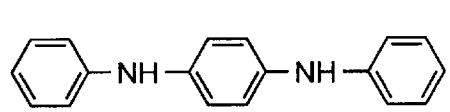
Figure 15:
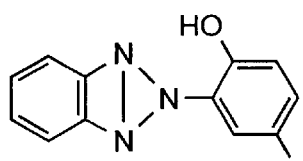
Figure 15:
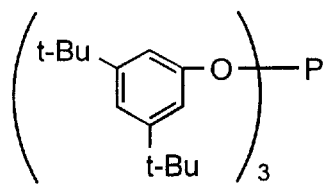
Figure 15:
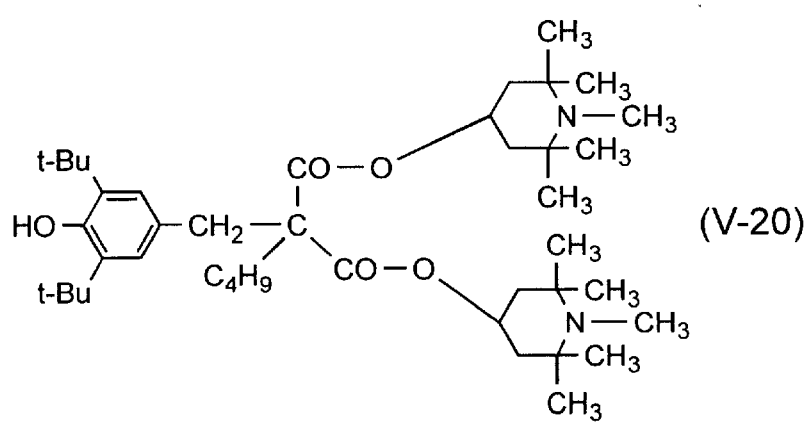
Figure 15:
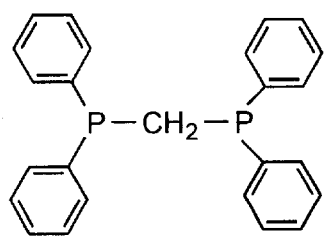
Figure 15:
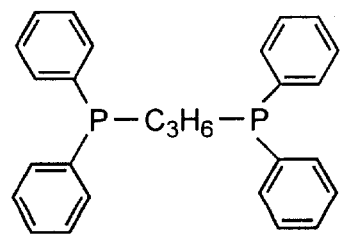
Figure 16:
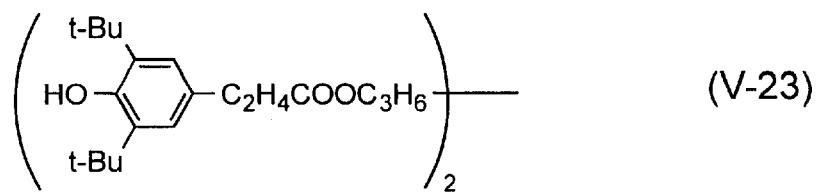
FIG. 16 are specific examples of antioxidants for the photosensitive body of the present invention.
Figure 16:
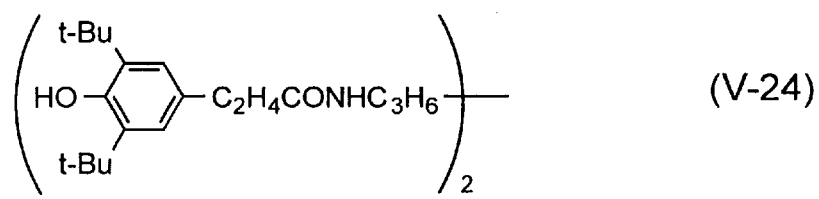
Figure 16:
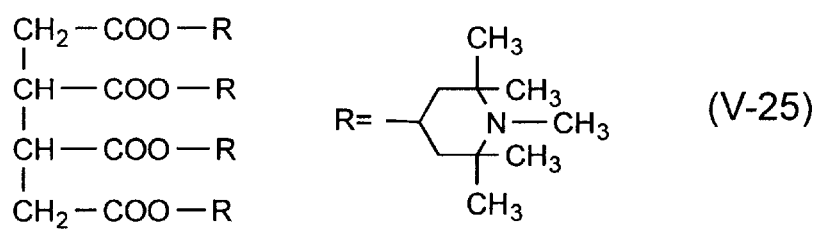
Figure 16:
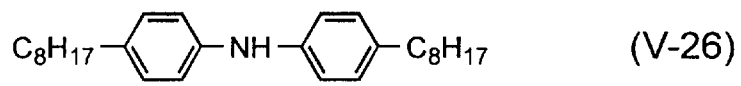
Figure 16:
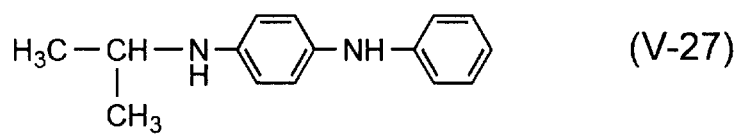
Figure 16:
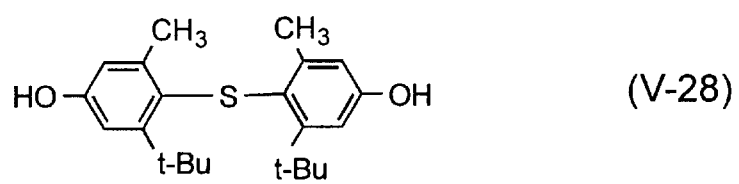
Figure 16:
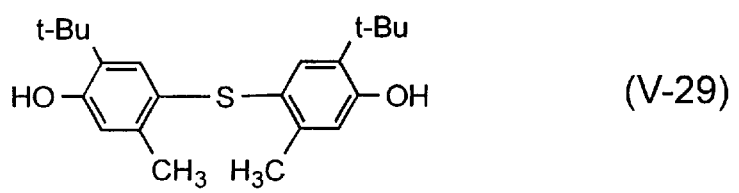

Fifty pts.wt. of the hydrazone compound shown in FIG. 10 as specific example III-1, 50 pts.wt. of the hydrazone compound shown in FIG. 10 as specific example III-2, 100 pts.wt. of bisphenol A-type-biphenyl copolymeric polycarbonate (ToughZ manufactured by Idemitsu Kosan Co., Ltd.), 5 pts.wt. of the hindered phenol compound shown in FIG. 13 as specific example V-2, and 1 pts.wt. of the butadiene derivative shown in FIG. 4 as specific example I-1 were dissolved into 700 pts.wt. of dichloromethane to provide a charge-transport coating liquid. The coating liquid was then coated onto the charge-generation layer in the same manner as described above. The coating layer was then dried at 90° C. for 30 minutes to form a charge-transport layer with a thickness of 20 µm.

Embodiment 10

A photosensitive body was produced in the same manner as in Embodiment 9 except for the use of the butadiene derivative shown in FIG. 4 by (I-3) instead of the butadiene derivative in Embodiment 9.

Embodiment 11

A photosensitive body was produced in the same manner as in Embodiment 9 except for the use of the butadiene derivative shown in FIG. 4 by (I-4) instead of the butadiene derivative in Embodiment 9.

Embodiment 12

A photosensitive body was produced in the same manner as in Embodiment 9 except for the use of the butadiene derivative shown in FIG. 4 by (I-5) instead of the butadiene derivative in Embodiment 9.

Embodiment 13

A photosensitive body was produced in the same manner as in Embodiment 9 except for the use of the butadiene derivative shown in FIG. 4 by (I-6) instead of the butadiene derivative in Embodiment 9.

Embodiment 14

A photosensitive body was produced in the same manner as in Embodiment 9 except for the use of the butadiene derivative shown in FIG. 5 by (I-11) instead of the butadiene derivative in Embodiment 9.

Embodiment 15

A photosensitive body was produced in the same manner as in Embodiment 9 except for the use of the butadiene derivative shown in FIG. 5 by (I-13) instead of the butadiene derivative in Embodiment 9.

Embodiment 16

A photosensitive body was produced in the same manner as in Embodiment 9 except for the use of the butadiene derivative shown in FIG. 5 by (I-14) instead of the butadiene derivative in Embodiment 9.

Embodiment 17

A photosensitive body was produced in the same manner as in Embodiment 9 except for the use of the bisazo compound shown in FIG. 7 by (II-7) instead of the charge-generation substance in Embodiment 9.

Embodiment 18

A photosensitive body was produced in the same manner as in Embodiment 9 except for the use of the bisazo compound shown in FIG. 9 by (II-24) instead of the charge-generation substance in Embodiment 9.

Embodiment 19

A photosensitive body was produced in the same manner as in Embodiment 9 except for the use of 50 pts.wt. of the hydrazone compound shown in FIG. 10 by (III-3) and 50 pts.wt. of the butadiene compound shown in FIG. 10 by (III-4) instead of the charge-transport substance in Embodiment 9.

Embodiment 20

Figure 11:
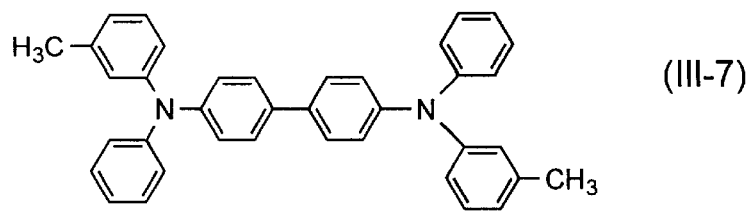
FIG. 11 are specific examples of compounds that are used in combination with the butadiene derivatives of Formula (I) according to the present invention.
Figure 11:
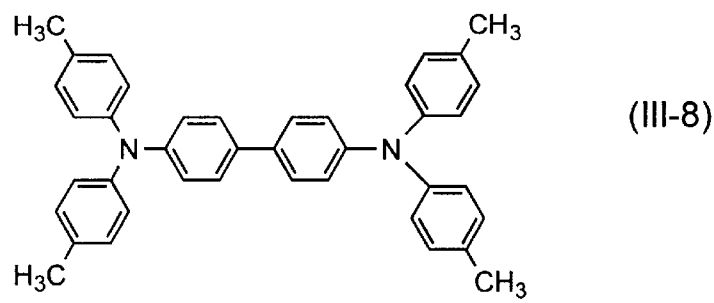
Figure 11:
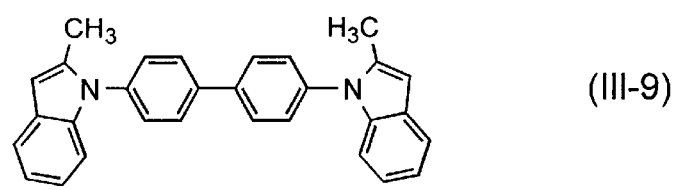
Figure 11:
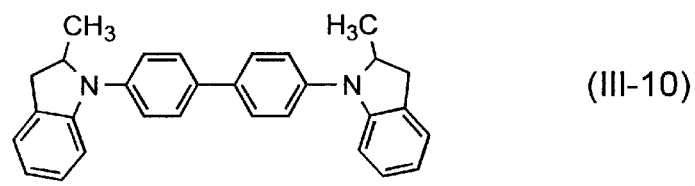
Figure 11:
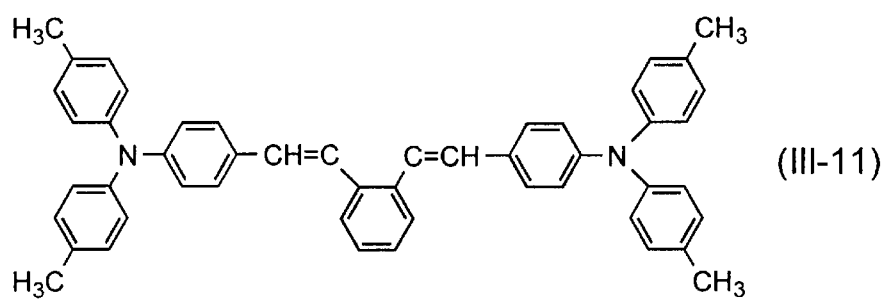
Figure 11:
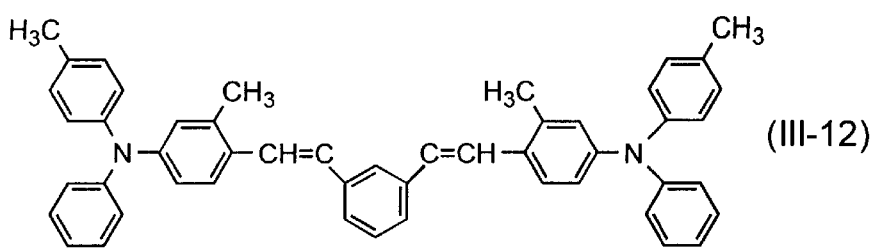

A photosensitive body was produced in the same manner as in Embodiment 9 except for the use of 50 pts.wt. of the diamine compound shown in FIG. 11 by (III-10) and 50 pts.wt. of the distyryl compound shown in FIG. 11 by (III-11) instead of the charge-transport substance in Embodiment 9.

Embodiment 21

Figure 12:
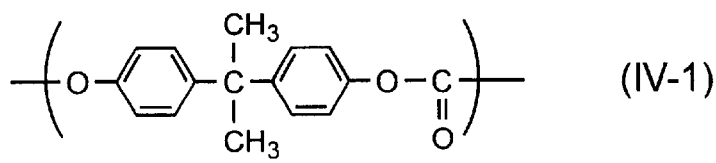
FIG. 12 are specific examples of polycarbonate resin binders for the charge transport layer for the photosensitive body of the present invention.
Figure 12:
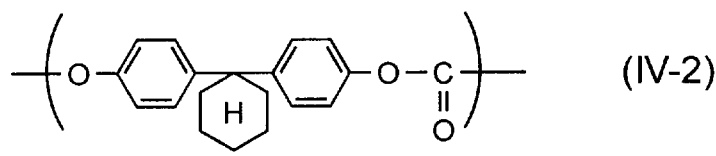
Figure 12:
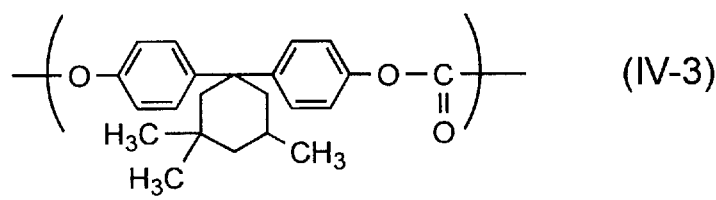
Figure 12:
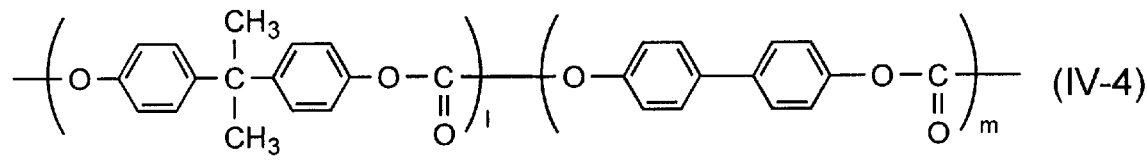
Figure 12:
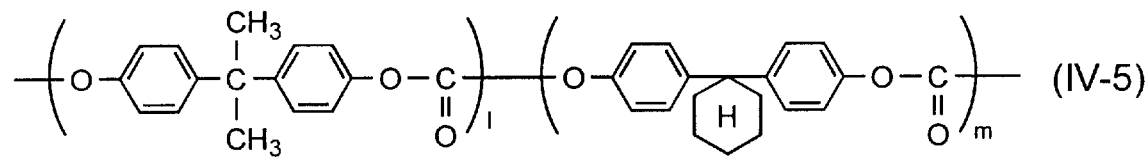
Figure 12:
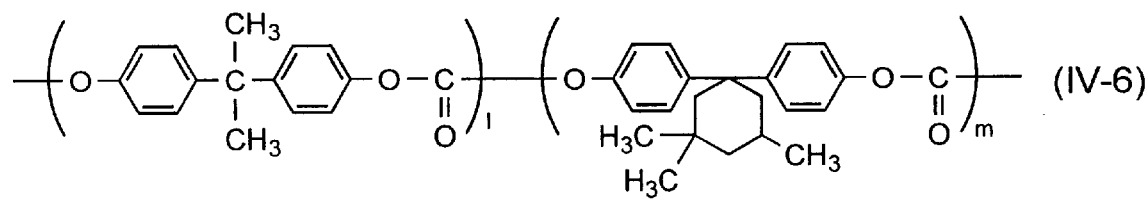
Figure 12:
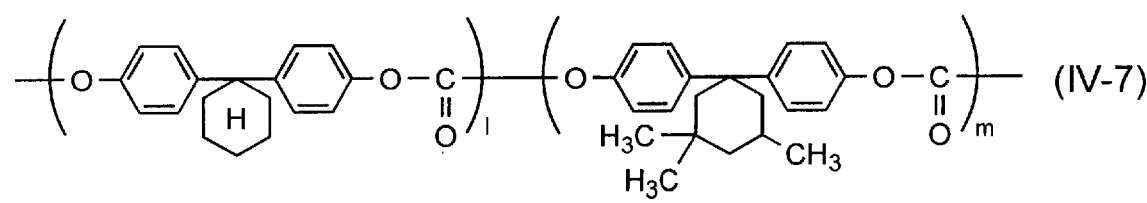

A photosensitive body was produced in the same manner as in Embodiment 9 except for the use of polycarbonate resin shown in FIG. 12 by (IV-2) instead of the resin of the charge-transport layer in Embodiment 9.

Embodiment 22

A photosensitive body was produced in the same manner as in Embodiment 9 except for the use of polycarbonate resin shown in FIG. 12 by (IV-6) instead of the resin of the charge-transport layer in Embodiment 9.

Embodiment 23

Figure 17:
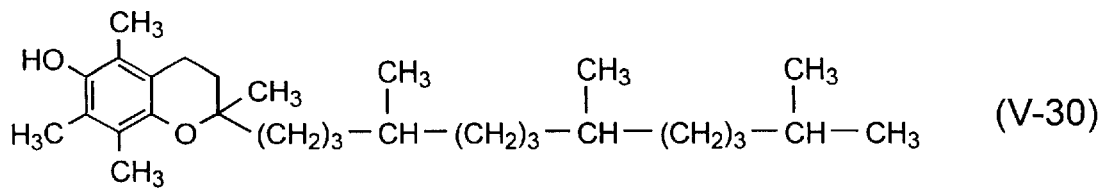
FIG. 17 are specific examples of antioxidants for the photosensitive body of the present invention.
Figure 17:
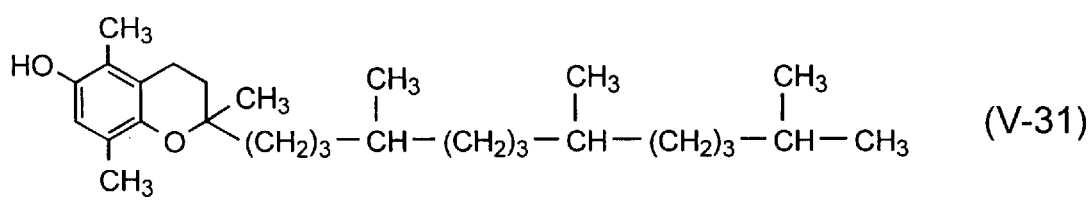
Figure 17:
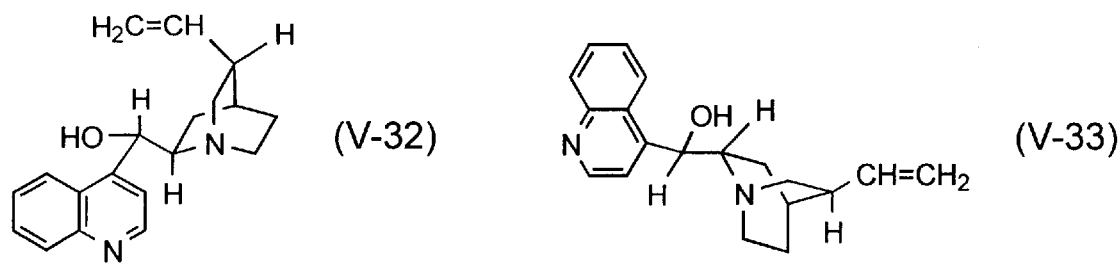
Figure 17:
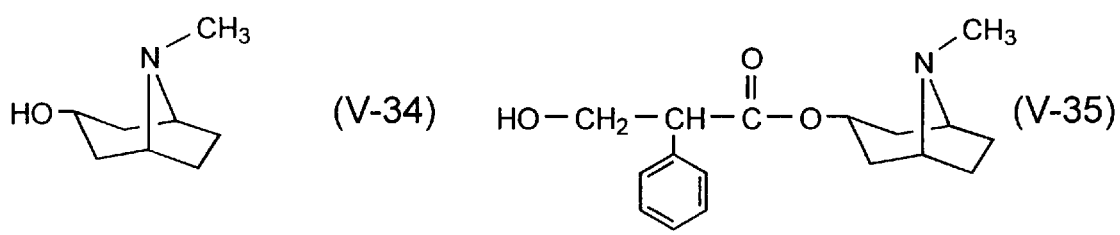
Figure 17:
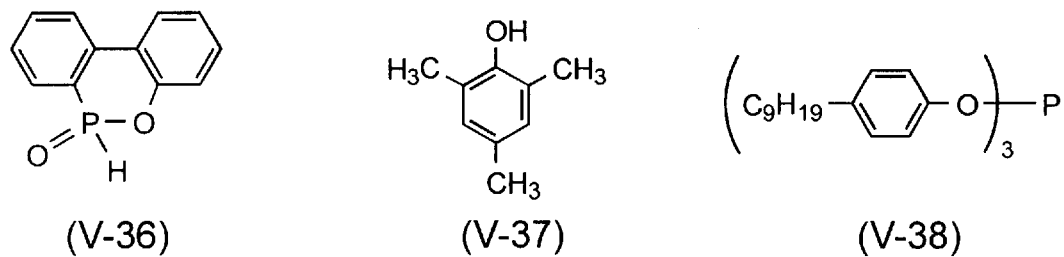
Figure 18:
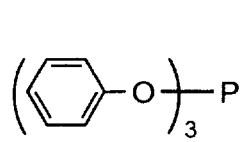
FIG. 18 are specific examples of antioxidants for the photosensitive body of the present invention.
Figure 18:
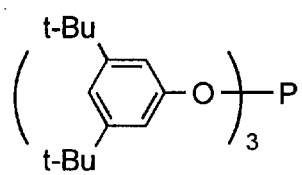
Figure 18:
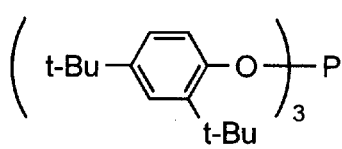
Figure 18:
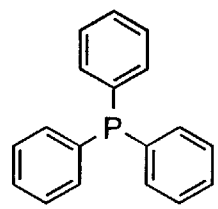
Figure 18:
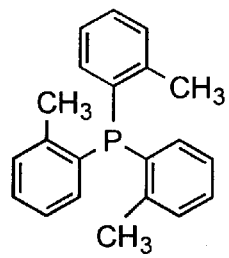
Figure 18:
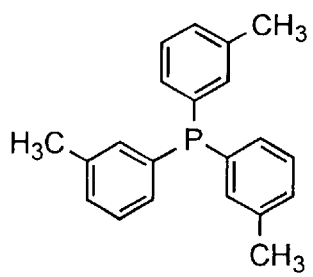
Figure 18:
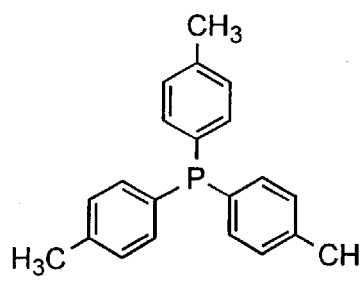

A photosensitive body was produced in the same manner as in Embodiment 9 except for the use of the compound shown in FIG. 17 by (V-30) as an additive to the charge-transport layer in Embodiment 9.

Embodiment 24

A photosensitive body was produced in the same manner as in Embodiment 9 except for the use of the compound shown in FIG. 17 by (V-37) as an additive to the charge-transport layer in Embodiment 9.

COMPARATIVE EXAMPLE 1

A photosensitive body was produced in the same manner as in Embodiment 9 except that the butadiene derivative in Embodiment 9 was not contained in the charge-transport layer.

COMPARATIVE EXAMPLE 2

A photosensitive body was produced in the same manner as in Embodiment 17 except that the butadiene derivative in Embodiment 17 was not contained in the charge-transport layer.

COMPARATIVE EXAMPLE 3

A photosensitive body was produced in the same manner as in Embodiment 19 except that the butadiene derivative in Embodiment 19 was not contained in the charge-transport layer.

COMPARATIVE EXAMPLE 4

A photosensitive body was produced in the same manner as in Embodiment 21 except that the butadiene derivative in Embodiment 21 was not contained in the charge-transport layer.

COMPARATIVE EXAMPLE 5

A photosensitive body was produced in the same manner as in Embodiment 23 except that the butadiene derivative in Embodiment 23 was not contained in the charge-transport layer.

Evaluation

The electrophotographic characteristics of the photosensitive bodies produced by the above embodiments and comparative examples were evaluated by the following methods. The electrophotographic characteristics were measured by using an electrostatic recording paper test apparatus.

The surfaces of the photosensitive bodies were negatively charged by executing −6.0 kV corona discharge for 10 seconds in a dark place, and then retained in the same place for 5 seconds with the corona discharge suspended. The surface potential was measured and the surface potential retention rate was determined 5 seconds later. The surfaces of the photosensitive bodies were then irradiated with white light at an illumination of 2 lx to determine the time needed (in seconds) until the surface potential decreased to half in order to obtain a half-value exposure $E_{1/2}$ (lux•S). The electrophotographic characteristics of the photosensitive bodies produced by Embodiments 9 to 24 and Comparative Examples 1 to 5 were then evaluated.

To evaluate the variation of the potential during repeated use, the outputs of charging, exposure, and electrostatic elimination mechanisms in an analog copier that uses a scorotron charging process and a two-component developing method were fixed. Various photosensitive bodies were mounted in this copier and the running test of 50,000 sheets of A3 paper was conducted in an atmosphere with normal temperature and humidity (20° C., 60 RH). By measuring the white paper potential (Vw) at the beginning of the test and black paper potential (Vb) at the end, the variation of the potential associated with the running was obtained (ΔVw, ΔVb). The results are shown in Table 2.

TABLE 2

| Reagent | Butadiene Cpd | Charge Generation Cpd | Charge Transport Cpd | Charge Transfer Binding Resin | Additive | Retention Rate 5 sec after Running VK5 (%) | Half-Value Exposure (lux*s) | Results of Running Tests Initial Potential Vw (V) | Vb (V) | Variation ΔVw (V) | ΔVb (V) |
|---|---|---|---|---|---|---|---|---|---|---|---|
| Embd 9  | I-1  | II-17 | III-1  | III-2  | IV-4 | V-2  | 98.0 | 0.87 | −47 | −605 | 2  | 0 |
| Embd 10 | I-3  | II-17 | III-1  | III-2  | IV-4 | V-2  | 96.5 | 0.90 | −45 | −603 | 3  | −1 |
| Embd 11 | I-4  | II-17 | III-1  | III-2  | IV-4 | V-2  | 96.4 | 0.85 | −45 | −605 | 1  | −3 |
| Embd 12 | I-5  | II-17 | III-1  | III-2  | IV-4 | V-2  | 95.4 | 0.86 | −44 | −603 | 3  | 0 |
| Embd 13 | I-6  | II-17 | III-1  | III-2  | IV-4 | V-2  | 96.7 | 0.87 | −48 | −604 | 6  | −2 |
| Embd 14 | I-11 | II-17 | III-1  | III-2  | IV-4 | V-2  | 97.0 | 0.88 | −47 | −605 | 1  | −3 |
| Embd 15 | I-13 | II-17 | III-1  | III-2  | IV-4 | V-2  | 96.0 | 0.89 | −45 | −607 | 3  | 0 |
| Embd 16 | I-14 | II-17 | III-1  | III-2  | IV-4 | V-2  | 96.2 | 0.90 | −45 | −605 | 3  | −3 |
| Embd 17 | I-1  | II-7  | III-1  | III-2  | IV-4 | V-2  | 96.5 | 0.86 | −45 | −607 | 5  | −3 |
| Embd 18 | I-1  | II-24 | III-1  | III-2  | IV-4 | V-2  | 96.7 | 0.85 | −43 | −605 | 5  | −4 |
| Embd 19 | I-1  | II-17 | III-3  | III-4  | IV-4 | V-2  | 97.2 | 0.85 | −45 | −605 | 3  | −4 |
| Embd 20 | I-1  | II-17 | III-10 | III-11 | IV-4 | V-2  | 98.0 | 0.88 | −45 | −607 | 5  | 0 |
| Embd 21 | I-1  | II-17 | III-1  | III-2  | IV-2 | V-2  | 97.0 | 0.85 | −45 | −605 | 1  | 0 |
| Embd 22 | I-1  | II-17 | III-1  | III-2  | IV-6 | V-2  | 95.9 | 0.88 | −44 | −607 | 5  | −1 |
| Embd 23 | I-1  | II-17 | III-1  | III-2  | IV-4 | V-30 | 97.0 | 0.85 | −45 | −605 | 2  | −5 |
| Embd 24 | I-1  | II-17 | III-1  | III-2  | IV-4 | V-37 | 98.0 | 0.85 | −45 | −605 | 4  | −2 |
| Comp 1  | —    | II-17 | III-1  | III-2  | IV-4 | V-2  | 96.0 | 0.99 | −48 | −610 | 82 | −26 |
| Comp 2  | —    | II-7  | III-1  | III-2  | IV-4 | V-2  | 97.0 | 0.95 | −46 | −608 | 55 | −19 |
| Comp 3  | —    | II-17 | III-3  | III-4  | IV-4 | V-2  | 95.5 | 1.03 | −45 | −605 | 59 | −28 |
| Comp 4  | —    | II-17 | III-1  | III-2  | IV-2 | V-2  | 97.4 | 1.03 | −44 | −609 | 76 | −16 |
| Comp 5  | —    | II-17 | III-1  | III-2  | IV-4 | V-30 | 95.2 | 1.01 | −45 | −605 | 93 | −18 |

The results of Embodiments 9 to 24 and Comparative Examples 1 to 5 clearly show that the photosensitive bodies produced without the addition of the butadiene derivative shown by Formula (I) of the present invention presented large variations in potential during the running test on the copier. Thus, these photosensitive bodies do not have excellent photosensitive characteristics of the present invention.

Furthermore, a comparison of Embodiment 9 with Embodiments 17 and 18 shows that stable photosensitive characteristics were obtained despite the replacement of the charge-generation substance. In addition, the same results were obtained when the charge-transport substance was replaced in Embodiments 19 and 20 and when the binding resin or antioxidant for the charge-transport layer was replaced in Embodiments 21 and 22 and Embodiments 23 and 24, respectively. This indicates that the photosensitive bodies according to the present invention can be widely used with various materials.

In addition to those photosensitive bodies for analog copiers that use an azo compound and that have been shown in the above embodiments, those photosensitive bodies for printers, digital copiers, or facsimiles that use the non-metallic phthalocyanine or titanyl phthalocyanine shown in FIG. 6 as examples (II-1) to (II-6) exhibited similar results when the photosensitive bodies, in which the butadiene derivative of the present invention was added to the charge-transport layer according to this invention, are used in actual printers, digital copiers, or facsimiles.

Although copiers using the scorotron and two-component developing methods have been described as a typical example in Embodiments 9 to 24, the photosensitive bodies in which the butadiene derivative is added to the charge-transport layer according to this invention also resulted in excellent repetition stability in various analog copiers, digital copiers, printers, and facsimile terminal equipment using various charging processes such as the corotron, charging brush, and charging roller methods, as well as the one-component developing method as described above.

The photosensitive body according to this invention uses the butadiene derivative shown by Formula (I) as the charge-transport substance on the conductive substrate in order to obtain high sensitivity and maintain stable characteristics during prolonged repeated use within an electrophotographic process.

The present invention also provides a photosensitive body that maintains high sensitivity and excellent electrical characteristics even when positively charged. In this case, a preferred charge-generation substance can be selected depending on the type of exposure light source used. For example, phthalocyanine or squarrylium compounds or certain types of bisazo compounds can be used to provide photosensitive bodies for use in copiers or semiconductor laser printers. The coating layer can be formed on the surface of the body as required to improve durability.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

Although only a single or few exemplary embodiments of this invention have been described in detail above, those skilled in the art will readily appreciate that many modifications are possible in the exemplary embodiment (s) without materially departing from the novel teachings and advantages of this invention. Accordingly, all such modifications are intended to be included within the scope of this invention as defined in the following claims, In the claims, means-plus-function clauses are intended to cover the structures described herein as performing the recited function and not only structural equivalents but also equivalent structures, This although a nail and screw may not be structural equivalents in that a nail relies entirely on friction between a wooden part and a cylindrical surface whereas a screw's helical surface positively engages the wooden part in the environment of fastening wooden parts, a nail and a screw may be equivalent structures.

What is claimed is:

1. A photosensitive body comprising:

a conductive substrate;

a photosensitive layer on said conductive substrate, said photosensitive layer includes a charge transport compound wherein said charge transport compound is a butadiene derivative described by a general formula (I):

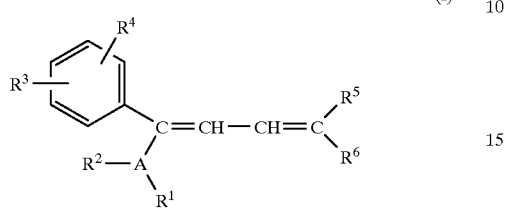

wherein A is a naphthyl group;

$R^1$ is a hydrogen atom, a halogen atom, an alkyl group with or without substitution, an alkoxy group, a nitro group, a cyano group, an aryl group with or without substitution, or a heterocyclic group with or without substitution;

$R^2$ is a halogen atom, an alkyl group with or without substitution, an alkoxy group, an alkylamino group, a nitro group, a cyano group, an aryl group with or without substitution, or a heterocyclic group with or without substitution;

$R^3$ is a halogen atom, an alkyl group with or without substitution, an alkoxy group, a nitro group, a cyano group, an aryl group with or without substitution, or a heterocyclic group with or without substitution;

$R^4$ is a halogen atom, an alkyl group with or without substitution, an alkoxy group, an alkylamino group, a nitro group, a cyano group, an aryl group with or without substitution, or a heterocyclic group with or without substitution;

$R^5$ is an alkoxycarbonyl group; and $R^6$ is an alkoxycarbonyl group.

2. A method to make a photosensitive body comprising:

forming a photosensitive layer on a substrate, said photosensitive layer including a charge transport compound wherein said charge transport compound is a butadiene derivative described by a general formula (I):

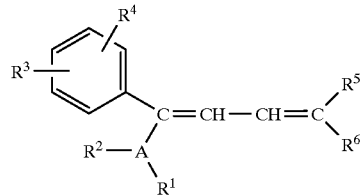

wherein A is a naphthyl group;

$R^1$ is a hydrogen atom, a halogen atom, an alkyl group with or without substitution, an alkoxy group, a nitro group, a cyano group, an aryl group with or without substitution, or a heterocyclic group with or without substitution;

$R^2$ is a halogen atom, an alkyl group with or without substitution, an alkoxy group, an alkylamino group, a nitro group, a cyano group, an aryl group with or without substitution, or a heterocyclic group with or without substitution;

$R^3$ is a halogen atom, an alkyl group with or without substitution, an alkoxy group, a nitro group, a cyano group, an aryl group with or without substitution, or a heterocyclic group with or without substitution;

$R^4$ is a halogen atom, an alkyl group with or without substitution, an alkoxy group, a nitro group, a cyano group, an aryl group with or without substitution, or a heterocyclic group with or without substitution;

$R^5$ is an alkoxycarbonyl group; and $R^6$ is an alkoxycarbonyl group.

* * * * *